United States Patent
Cai et al.

(10) Patent No.: US 11,371,065 B2
(45) Date of Patent: Jun. 28, 2022

(54) GENETICALLY ENGINEERED STRAIN

(71) Applicant: Jiangnan University, Wuxi (CN)

(72) Inventors: Yujie Cai, Wuxi (CN); Jinbin Liu, Wuxi (CN); Tianzhen Xiong, Wuxi (CN); Yanrui Ding, Wuxi (CN); Yajun Bai, Wuxi (CN); Xiaohui Zheng, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 16/205,497

(22) Filed: Nov. 30, 2018

(65) Prior Publication Data

US 2019/0136269 A1   May 9, 2019

Related U.S. Application Data

(63) Continuation of application No. PCT/CN2017/110338, filed on Nov. 10, 2017.

(30) Foreign Application Priority Data

Aug. 4, 2017 (CN) .......................... 201710659225.1

(51) Int. Cl.
| | | |
|---|---|---|
| *C12N 1/21* | (2006.01) | |
| *C12N 9/02* | (2006.01) | |
| *C12N 9/88* | (2006.01) | |
| *C12N 9/04* | (2006.01) | |
| *C12P 7/22* | (2006.01) | |
| *C12N 15/70* | (2006.01) | |
| *C12N 9/06* | (2006.01) | |
| *C12N 1/20* | (2006.01) | |
| *C12P 7/42* | (2006.01) | |

(52) U.S. Cl.
CPC .................. *C12P 7/22* (2013.01); *C12N 1/20* (2013.01); *C12N 9/0006* (2013.01); *C12N 9/0008* (2013.01); *C12N 9/0022* (2013.01); *C12N 15/70* (2013.01); *C12P 7/42* (2013.01); *C12Y 101/01001* (2013.01); *C12Y 102/01002* (2013.01); *C12Y 102/04004* (2013.01); *C12Y 104/03002* (2013.01)

(58) Field of Classification Search
None
See application file for complete search history.

(56) References Cited

FOREIGN PATENT DOCUMENTS

| CN | 106566794 A | 4/2017 |
|---|---|---|
| WO | 2004006657 A1 | 1/2004 |

OTHER PUBLICATIONS

Guo et al., "Mini-review: In vitro Metabolic Engineering for Biomanufacturing of High-value Products", Comp. Struct. Biotechnol. J. 15:161-167, 2017 (Year: 2017).*
Kim et al., "Current Status of Microbial Phenylethanoid Biosynthesis", J. Microbiol. Biotechnol. 28:1225-1232, 2018 (Year: 2018).*
Guo et al., "Metabolic engineering of *Escherichia coli* for production of 2-Phenylethylacetate from L-phenylalanine", MicrobiologyOpen 2017:e486, Apr. 2017, 5 pages (Year: 2017).*
Hou et al., "Production of phenylpyruvic acid from L-phenylalanine using an L-amino acid deaminase from Proteus mirabilis: comparison of enzymatic and whole-cell biotransformation approaches", Appl. Microbiol. Biotechnol. 99:891-8402, 2015 (Year: 2015).*
Cleton-Jansen et al., J. Bacteriol. 172:6308-6315, 1990 (Year: 1990).*
GenBank Database Accession No. CAQ34616, "predicted alcohol dehydrogenase, Zn-dependent and NAD(P)-binding [*Escherichia coli* BL21 (DE3)]", Feb. 2015, 2 pages (Year: 2015).*
GenBank Database Accession No. ACLE01000000, "Proteus mirabilis ATCC 29906, whole genome shotgun sequencing project", Sep. 2013, 2 pages (Year: 2013).*
GenBank Database Accession No. KST89287, "Pyruvate decarboxylase Alpha-keto-acid decarboxylase [*Lactococcus lactis* subsp. *lactis*]", Dec. 2015, 2 pages (Year: 2015).*
Pongtharangkul et al., AMB Expr. 5:68, 2015, 12 pages (Year: 2015).*
GenBank Database Accession No. AIW32463, "sugar dehydrogenase [Bacillus subtilis]", Nov. 2014, 2 pages (Year: 2014).*
Tolia et al., "Strategies for protein coexpression in *Escherichia coli*", Nat. Methods 3:55-64, 2006 (Year: 2006).*
Liu et al., J. Agric. Food Chem. 66:3498-3504, 2018 (Year: 2018).*
Ju et al., "Crystal structure of a membrane-bound L-amino acid deaminase from Proteus vulgaris", J. Struct. Biol. 195:306, 315, 2016 (Year: 2016).*
Daisuke Koma, et. al. Production of Aromatic Compounds by Metabolically Engineered *Escherichia coli* with an Expanded Shikimate Pathway. Applied and enviromental Microbiology, vol. 8, No. 17, p. 6203, Sep. 2012.
Jin-oh Baek, et. al. Expression and characterizatin of a second L-amino acid deaminase isolated from proteus mirabilis in *Escherichia coli*, Journal of Basic Microbiology, vol. 2, p. 129-135, Feb. 7, 2011.

* cited by examiner

*Primary Examiner* — David Steadman
(74) *Attorney, Agent, or Firm* — IPro, PLLC

(57) ABSTRACT

The present disclosure discloses a genetically engineered strain, belonging to the technical field of bioengineering. L-amino acid oxidase genes, α-keto acid decarboxylase genes, alcohol dehydrogenase genes, and enzyme genes capable of reducing NAD(P) to NAD(P)H are introduced into the genetically engineered strain of the present disclosure. The present disclosure further discloses a construction method and application of a recombinant *Escherichia coli* genetically engineered strain. When being applied to the biosynthesis of phenylethanoids, the method of the present disclosure has the characteristics of simple operation, low cost, and high synthesis efficiency and optical purity of the product, and has good industrialization prospects.

7 Claims, No Drawings
Specification includes a Sequence Listing.

GENETICALLY ENGINEERED STRAIN

REFERENCE TO SEQUENCE LISTING

The instant application contains a Sequence Listing in ASCII format as a file named seq-new.txt, created on Aug. 24, 2021, of 48 kB in size, and which is hereby incorporated by reference in its entirety.

TECHNICAL FIELD

The present disclosure relates to a genetically engineered strain, belonging to the technical field of bioengineering.

BACKGROUND

Phenylethanoids mainly have three structural analogs: 2-phenylethanol (β-phenylethanol), tyrosol (p-hydroxyphenylethanol, tyrosol, 4-hydroxyphenylethanol, 2-(4-hydroxyphenyl)ethanol), hydroxytyrosol (3,4-dihydroxyphenylethanol, hydroxytyrosol, 3,4-dihydroxyphenylethanol, 2-(3,4-dihydroxyphenyl)ethanol), which are all L-α-aromatic amino acid derivatives. 2-Phenylethanol is an aromatic alcohol with a delicate rose scent and is widely used in food, medicines, cosmetics, tobacco and daily chemicals. It is not only the basic component of all rose scent aromas, but also has synergetic and synergistic effects, and is a component required for a variety of fragrance formulae. Tyrosol is the core of the salidroside molecule, has good oxidation resistance, and is also an important pharmaceutical intermediate. It is mainly used in the synthesis of cardiovascular drugs, such as Metoprolol, Bxolol and the like. Hydroxytyrosol is regarded as one of the most powerful antioxidants and can eliminate free radicals in the body, restore the health of the internal organs of the human body, prevent brain failure and delay aging.

These compounds are currently produced by methods such as plant extraction, chemical synthesis, microbiological and the like. Chemical methods have been successful in the synthesis of 2-phenylethanol, tyrosol and hydroxytyrosol (Chinese patents 200880002426.3, 201310183569.1, 200910098983.6). Since these compounds are important food or health care raw materials, chemically synthesized products are not liked by people. These products currently on the market are mainly extracted from plants. For example, Chinese patent 201510625623.2 discloses a method for extracting high-purity 2-phenylethanol from rose petals; Chinese patent 201410743409.2 discloses a method for preparing high-purity tyrosol from *Rhodiola crenulata*; And Chinese patent 201710195462.7 discloses a method for extracting hydroxytyrosol from olive leaves. Due to the limitations of plant resources and contents thereof, these products are expensive, so the production by microbiological methods has received extensive attention.

L-phenylalanine, L-tyrosine, and L-dopa may be subjected to deamination, decarboxylation and aldehyde group reduction to form 2-phenylethanol, tyrosol and hydroxytyrosol. Based on this metabolic principle, several microbiological production methods have been developed.

Yeast has a metabolic pathway for the de novo synthesis of 2-phenylethanol, and can also directly transform L-phenylalanine to 2-phenylethanol through an amino acid catabolic pathway. As early as 1907, Ehrlich added L-phenylalanine in a yeast medium, so that the yield of 2-phenylethanol was greatly increased (Ber Dtsch Chem Ges, 1907.40:1027-1047). Chinese patents 02137575.5, 200710066884.0, 200810071807.9, 200910049170.8, 200910049565.8, 201310243384.5, 201410661174.2 and 201610256845.6 all disclose strains and methods for producing 2-phenylethanol by transforming L-phenylalanine with yeast. Romagnoli has developed a method for producing 2-phenylethanol by deleting yeast aromatic amino acid transaminase and using glucose as a substrate, the yield is about 3 mM, and a small amount of tyrosol is also produced (Deletion of the *Saccharomyces cerevisiae* Aro8 Gene, Encoding an Aromatic Amino Acid Transaminase, Enhances Phenylethanol Production from Glucose. Yeast, 2015,32(1): 29-45). Since the yeast grows slowly and consumes part of L-phenylalanine during the transformation process, the yield of the 2-phenylethanol is lower and the cost is higher.

There are still other methods for preparing 2-phenylethanol by *Enterobacter* sp. (De-Novo Synthesis of 2-Phenylethanol by *Enterobacter* Sp CGMCC 5087. BMC Biotechnology, 2014,14) or the submerged fermentation technique of *Antrodia camphorata* (Chinese patent 201410041209.2), but they have lower efficiency than the yeast.

*Escherichia coli* grows faster and is a better option for genetically engineered bacteria. Chinese patent 201210276491.3 over-expresses phenylpyruvate decarboxylase and alcohol dehydrogenase in L-phenylalanine high-yield *Escherichia coli* to achieve a high yield of 2-phenylethanol, but the over-expressed 2 enzymes disturb the metabolism of *Escherichia coli* grown by de novo synthesis of glucose, so the yield can only reach 130 mg/L. Chinese patent 201510650028.4 co-expresses 4 enzymes in *Escherichia coli*, namely aromatic amino acid aminotransferase, exogenous phenylpyruvate decarboxylase, phenyl alcohol dehydrogenase and glutamate dehydrogenase, for whole cell transformation of L-phenylalanine to produce 2-phenylethanol; due to the low concentration of α-ketoglutaric acid in the cells, it is difficult to provide sufficient ammonia receptors; when the α-ketoglutaric acid is added to the transformation system, the highest yield can be obtained, and glutamic acid can also be added to significantly increase the yield; and it is clear that the addition of other compounds will increase the cost of transformation and will also increase the complexity of the transformation and purification operations. Chinese patent 201610464256.7 discloses a non-cellular biosynthesis method, by which separately expressed transaminase, phenylpyruvate decarboxylase and alcohol dehydrogenase are co-fixed or L-phenylalanine is transformed in a solution volume to produce 2-phenylethanol; and it is found from the published documents that the system lacks sufficient ammonia receptors and NADH, so the process can not easily implement production. Chinese patent 201710256900.6 discloses: mixing three kinds of *Escherichia coli* wet cells for respectively expressing phenylalanine dehydrogenase, 2-keto acid decarboxylase and alcohol dehydrogenase, adding coenzymes TPP and NAD, and controlling temperature and pH for transforming L-phenylalanine; and in this method, the NAD and TPP are expensive and will be decomposed and fail after reacting for certain time, the three enzymes need to be separately cultured, which greatly increases the reaction cost, and the independent cells also affect the NAD shuttle between cells to achieve coenzyme regeneration, so the transformation reaction is difficult to continue.

Chinese patent 201310133238.7 discloses a method for producing tyrosol from tyrosine or glucose by over-expressing 4-hydroxyphenyl decarboxylase derived from *Saccharomyces cerevisiae* in *Escherichia coli* and knocking out the phenylacetaldehyde dehydrogenase gene; however, when the tyrosine is used as a substrate, this strain lacks an effective deamination system; when the glucose is used for de novo synthesis, the tyrosol is toxic to the cells, affecting cell growth and product synthesis; and therefore, this strain is difficult to achieve efficient production of tyrosol. 201510242626.8 discloses a method of over-expressing a monooxygenase gene cluster HpaBC derived from *Escherichia coli* in *Escherichia coli* and realizing de novo synthesis of hydroxytyrosol from glucose; the main disadvantage of this scheme is that the hydroxytyrosol is toxic to the cells and has the lower expression level of HpaBC; and therefore, the efficiency of producing hydroxytyrosol is more difficult to increase. Chinese patent 201710091999.9 discloses an *Escherichia coli* which over-expresses pyruvate decarboxylase and aromatic amino acid aminotransferase derived from *Saccharomyces cerevisiae* and application of the bacterium for producing tyrosol by whole cell transformation of L-tyrosine; And it is clear that the bacterium lacks sufficient ammonia receptors and a good aldehyde reduction system, so the yield is low. Chung et al., by over-expressing plant-derived aromatic aldehyde synthases in *Escherichia coli*, converting L-tyrosine into p-hydroxyphenylacetaldehyde in one step, and then producing tyrosol from the reduction system inside *Escherichia coli*; and in addition, over-expression of HpaBC achieved hydroxytyrosol, but the low expression efficiency of plant genes in *Escherichia coli* affected the whole cell transformation effect (Production of Three Phenylethanoids, Tyrosol, Hydroxytyrosol, and Salidroside, Using Plant Genes Expressing in *Escherichia coli*. Scientific Reports, 2017).

Currently, multi-enzyme tandem whole-cell catalyzed simple precursor generation of high-added-value products has been widely used (Constructing Biocatalytic Cascades: In Vitro and in Vivo Approaches to de Novo Multi-Enzyme Pathways, ACS Catal., 2017, 7(1), 710-724), and efficient transformation of inexpensive substrates by whole cells is sometimes more cost effective than de novo synthesis with glucose.

Based on the defects in various current methods, the present disclosure constructs a multi-enzyme co-expressed *Escherichia coli*, which realizes the whole cell catalytic transformation of aromatic L-α-amino acids and can respectively catalyze L-phenylalanine, L-tyrosine and L-dopa to produce 2-phenylethanol, tyrosol and hydroxytyrosol.

SUMMARY

Based on the defects of various current methods, the present disclosure provides a recombinant *Escherichia coli* strain capable of producing Phenylethanoids at low cost. At the same time, the present disclosure aims to solve the technical problems of the construction and application of the strain.

A first object of the present disclosure is to provide a recombinant *Escherichia coli* strain capable of producing Phenylethanoids at low cost; and the recombinant *Escherichia coli* strain simultaneously expresses 4 enzymes, namely L-amino acid oxidase, α-keto acid decarboxylase, alcohol dehydrogenase, and an enzyme capable of reducing NAD(P) to NAD(P)H.

In an implementation, the L-amino acid oxidase is from *Proteus mirabilis* ATCC 29906 or *Cosenzaea myxofaciens* ATCC 19692.

In an implementation, the amino acid sequence of the L-amino acid oxidase is a sequence of which the accession NO. in NCBI is WP_004244224.1 (SEQ ID NO:1) or OAT30925.1 (SEQ ID NO:2) and which is hereby incorporated by reference in its entirety.

In an implementation, the nucleotide sequence of the L-amino acid oxidase is a sequence of which the accession NO. in NCBI is NZ_GG668576 REGION: 1350390 . . . 1351805 (SEQ ID NO:3) and which is hereby incorporated by reference in its entirety, or LXEN01000066 REGION: 20563 . . . 21963 (SEQ ID NO:4) and which is hereby incorporated by reference in its entirety.

In an implementation, the α-keto acid decarboxylase is from *Proteus mirabilis* ATCC 29906 or *Lactococcus lactis* ATCC 19435.

In an implementation, the amino acid sequence of the α-keto acid decarboxylase is a sequence of which the accession NO. in NCBI is BC_004247067.1 (SEQ ID NO:5) and which is hereby incorporated by reference in its entirety, or WP_025016816.1 (SEQ ID NO:6) and which is hereby incorporated by reference in its entirety.

In an implementation, the nucleotide sequence of the α-keto acid decarboxylase is a sequence of which the accession NO. in NCBI is NZ_GG668593 REGION: 50463 . . . 52112 (SEQ ID NO:7) and which is hereby incorporated by reference in its entirety, or NZ_LKLC01000008 REGION: 208327 . . . 209973 (SEQ ID NO:8) and which is hereby incorporated by reference in its entirety.

In an implementation, the alcohol dehydrogenase is from *Escherichia coli* BL21(DE3).

In an implementation, the amino acid sequence of the alcohol dehydrogenase is a sequence of which the accession NO. in NCBI is WP_001318460.1 (SEQ ID NO:9) and which is hereby incorporated by reference in its entirety, or WP_000692754.1 (SEQ ID NO:10) and which is hereby incorporated by reference in its entirety.

In an implementation, the nucleotide sequence of the alcohol dehydrogenase is a sequence of which the accession NO. in NCBI is NC_012892 REGION: 4406777 . . . 4407796 (SEQ ID NO:11) and which is hereby incorporated by reference in its entirety, or NC_012892 REGION: 312506 . . . 313555 (SEQ ID NO:12) and which is hereby incorporated by reference in its entirety.

In an implementation, the enzyme capable of reducing NAD(P) to NAD(P)H is formate dehydrogenase, glucose dehydrogenase or phosphite dehydrogenase.

In an implementation, the enzyme capable of reducing NAD(P) to NAD(P)H is formate dehydrogenase from *Komagataella phaffii* ATCC 76273, glucose dehydrogenase from *Bacillus subtilis* ATCC 13952, or phosphite dehydrogenase from *Pseudomonas abietaniphila* ATCC 700689.

In an implementation, the amino acid sequence of the enzyme capable of reducing NAD(P) is a sequence of which the accession NO. in NCBI is AOA63544.1 (SEQ ID NO:13) and which is hereby incorporated by reference in its entirety, WP_013351020.1 (SEQ ID NO:14) and which is hereby incorporated by reference in its entirety or WP_003118429.1 (SEQ ID NO:15) and which is hereby incorporated by reference in its entirety.

In an implementation, the nucleotide sequence of the enzyme capable of reducing NAD(P) is a sequence of which the accession NO. in NCBI is CP014710 REGION: 1836993 . . . 1838090 (SEQ ID NO:16) and which is hereby incorporated by reference in its entirety, NZ_CP009748 REGION: 386154 . . . 38693 (SEQ ID NO:17) and which is hereby incorporated by reference in its entirety, or NZ_FNCO01000027 REGION: 29475 . . . 30485 (SEQ ID NO:18) and which is hereby incorporated by reference in its entirety.

In an implementation, the recombinant *Escherichia coli* strain co-expresses genes encoding the 4 enzymes using double plasmids pRSFDuet-1 and pETDuet-1; and the pRSFDuet-1 is loaded with L-amino acid oxidase genes and α-keto acid decarboxylase genes, and the pETDuet-1 is loaded with alcohol dehydrogenase genes and enzyme genes capable of reducing NAD(P).

In an implementation, the recombinant *Escherichia coli* strain is obtained by transforming 2 co-expressed recombinant plasmids into a host *Escherichia coli* B21.

A second object of the present disclosure is to provide a method for producing phenylethanoids, which utilizes the recombinant *Escherichia coli* strain of the present disclosure.

In an implementation, the phenylethanoids is any of 2-phenylethanol, tyrosol and hydroxytyrosol.

In an implementation, the substrate for producing the phenylethanoids is any one or more of L-phenylalanine, L-tyrosine and L-dopa.

In an implementation, the production of the phenylethanoids is carried out by whole cell transformation.

In an implementation, a whole cell transformation production system comprises a fresh cell wet weight of 10-200 g/L, a substrate concentration of 0.5-20 g/L, a hydrogen donor concentration of 1-20 g/L, and a pH of 4.0-8.0; and the reaction is carried out at 15-40° C. for 0.5-48 hours.

In an implementation, the method for obtaining cells comprises: inoculating the recombinant *Escherichia coli* strain into an LB fermentation medium, and after the $OD_{600}$ of the cells reaches 0.6-0.8, adding IPTG to induce expression; after the induction of expression is completed, collecting the cells by centrifugation.

In an implementation, when the constructed three enzyme co-expressed plasmid contains glucose dehydrogenase, the hydrogen donor is glucose; when the constructed three enzyme co-expressed plasmid contains formate dehydrogenase, the hydrogen donor is sodium formate; and when the constructed three enzyme co-expressed plasmid contains phosphite dehydrogenase, the hydrogen donor is phosphorous acid.

Beneficial Effects of the Disclosure:

The present disclosure constructs a novel four-enzyme co-expressed *Escherichia coli* engineered strain, which can be applied to the production of phenylethanoids. The L-amino acid oxidase, α-keto acid decarboxylase and alcohol dehydrogenase selected by the disclosure have the characteristics of poor substrate specificity and high activity, so the same engineered strain can produce a variety of phenylethanoids under the condition of using aromatic-α-amino acids, and can also be used for producing derivatized alcohols of other amino acids. The production process is simple and the raw materials are easily available, so the strain has good industrial application prospects.

DETAILED DESCRIPTION

The functional core of the *Escherichia coli* of the present disclosure is that it can simultaneously express 4 enzymes, namely L-amino acid oxidase, α-keto acid decarboxylase, alcohol dehydrogenase, and an enzyme capable of reducing NAD(P) to NAD(P)H. The principle is as follows: in the whole cells of the engineered strain, the L-amino acid oxidase oxidizes L-phenylalanine, L-tyrosine and L-dopa to the corresponding phenylpyruvic acid, p-hydroxyphenylpyruvic acid and 3,4-dihydroxyphenylpyruvic acid; subsequently, phenylacetaldehyde, p-hydroxyphenylacetaldehyde and 3,4-dihydroxyphenylacetaldehyde are produced under the action of the α-keto acid decarboxylase; the alcohol dehydrogenase and the enzyme capable of reducing NAD(P) to NAD(P)H constitute NAD coenzyme cyclic regeneration system, and the aldehyde is reduced by the alcohol dehydrogenase; and a whole-cell four-enzyme cascade one-step method is adopted to respectively transform L-phenylalanine, L-tyrosine and L-dopa into 2-phenylethanol, tyrosol and hydroxytyrosol.

In order to solve the above technical problems, the technical solutions adopted by the present disclosure are as follows:

1. Strains and Plasmids Involved in the Present Disclosure

*Proteus mirabilis* ATCC 29906, *Cosenzaea myxofaciens* ATCC 19692, *Lactococcus lactis* ATCC 19435, *Komagataella phaffii* ATCC 76273, *Bacillus subtilis* ATCC 13952 and *Pseudomonas abietaniphila* ATCC 700689 purchased from the American Type Culture Collection (ATCC). pRSF-Duet-1 plasmid, pETDuet-1 plasmid, *Escherichia coli* BL21 (DE3) and *Escherichia coli* BL21 DH5a purchased from Novagen Company.

2. Selection of Enzymes (1) Selection of L-Amino Acid Oxidases

L-amino acid oxidases are widely found in bacteria, fungi, mammalian cells, snake venom, insect toxins and algae (L-amino acid oxidase as biocatalyst: a dream too far? Appl. Microbiol. Biotechnol. 2013, 97:9323-41). L-amino acid oxidases transfer hydrogen from a amino and $C^\alpha$ to FAD, most of which utilize molecular oxygen to directly oxidize reduced FAD to regenerate oxidized FAD and generate hydrogen peroxide at the same time, and catalase must be added during this process to eliminate the toxicity of the hydrogen peroxide. There is also a type of L-amino acid oxidase associated with the electron transport chain on the cell membrane. The electrons are transferred to the cytochrome oxidase through a respiratory chain, and the molecular oxygen is reduced to water, so that no hydrogen peroxide is formed. This enzyme mainly exists in *Proteus* sp., *Providencia* sp., *Morganella* sp., etc. (Crystal structure of a membrane-bound L-amino acid deaminase from *Proteus vulgaris*. J. Struct. Biol. 2016, 195:306-15). In the present disclosure, two L-amino acid oxidases which do not produce hydrogen peroxide are selected, and the L-amino acid oxidase genes pmaao and cmaao are cloned from *Proteus mirabilis* ATCC 29906 and *Cosenzaea myxofaciens* ATCC 19692 respectively; the nucleotide sequences thereof are sequences of which the Accession NO. in NCBI are NZ_GG668576 REGION: 1350390 . . . 1351805 (SEQ ID NO:3) and LXEN01000066 REGION: 20563 . . . 21963 (SEQ ID NO:4), and the amino acid sequences are as shown in WP_004244224.1 (SEQ ID NO:1) and OAT30925.1 (SEQ ID NO:2); And these enzymes both have the characteristics of broad substrates and high activity.

(2) Selection of α-Keto Acid Decarboxylases

According to literature reports, the α-keto acid decarboxylases, which are derived from bacteria and have high activity on aromatic keto acids, are selected, and have the characteristic of being better expressed in *Escherichia coli* than enzymes derived from yeast or plants in other patents. The α-keto acid decarboxylase genes pmkdc and llkdc are cloned from *Proteus mirabilis* ATCC 29906 and *Lactococcus lactis* ATCC 19435 respectively; And the amino acid sequences thereof are sequences of which the accession NO. in NCBI are WP_004247067.1 (SEQ ID NO:5) and WP_025016816.1 (SEQ ID NO:6), and the nucleotide sequences are sequences of which the Accession NO. in NCBI are NZ_GG668593 REGION: 50463 . . . 52112 (SEQ ID NO:7) and NZ_LKLC01000008 REGION: 208327 . . . 209973 (SEQ ID NO:8).

(3) Selection of Alcohol Dehydrogenases

Alcohol dehydrogenases are widely found in various types of bacteria. According to reports, *Escherichia coli* itself also contains a wide variety of alcohol dehydrogenases having wide substrates (Production of aromatic compounds by metabolically engineered *Escherichia coli* with an expanded shikimate pathway, Appl. Environ. Microbiol. 2012 78(17), 6203-6216). Therefore, two alcohol dehydrogenase genes, ecadh1 and ecadh2, are cloned directly from *Escherichia coli* BL21 (DE3). The amino acid sequences of the alcohol dehydrogenase are sequences of which the accession NO. in NCBI are WP_001318460.1 (SEQ ID NO:9) and WP_000692754.1 (SEQ ID NO:10), and the nucleotide sequences are sequences of which the accession NO. in NCBI are NC_012892 REGION: 4406777 . . . 4407796 (SEQ ID NO:11) and NC_012892 REGION: 312506 . . . 313555 (SEQ ID NO:12), thereby being more beneficial to the over-expression of the alcohol dehydrogenases in *Escherichia coli*.

(4) Selection of the Enzyme Capable of Reducing NAD (P)

In the biotransformation reaction, the alcohol dehydrogenase requires NADH and/or NADPH as a coenzyme. The present disclosure obtains the formate dehydrogenase gene kpfdh from *Komagataella phaffii* ATCC 76273, the glucose dehydrogenase gene bsgdh from *Bacillus subtilis* ATCC 13952 and the phosphite dehydrogenase gene papdh from *Pseudomonas abietaniphila* ATCC 700689. The amino acid sequence is a sequence of which the accession NO. in NCBI is AOA63544.1 (SEQ ID NO:13), WP_013351020.1 (SEQ ID NO:14) and WP_003118429.1 (SEQ ID NO:15), and the nucleotide sequence is a sequence of which the accession NO. in NCBI is CP014710 REGION: 1836993 . . . 1838090 (SEQ ID NO:16), NZ_CP009748 REGION: 386154 . . . 38693 (SEQ ID NO:17) or NZ_FNCO01000027 REGION: 29475 . . . 30485 (SEQ ID NO:18).

3. Construction of Four Enzymes Co-Expressed System

Any enzyme is selected from each type of the L-amino acid oxidases, α-keto acid decarboxylases, alcohol dehydrogenases and enzymes capable of reducing NAD(P) and subjected to four enzyme co-expression. At present, there are various methods for *Escherichia coli* multi-gene co-expression (*E. coli* multi-gene co-expression strategy, Journal of Chinese Biotechnology, 2012, 32(4):117-122). The present disclosure uses double plasmids pRSFDuet-1 and pETDuet-1 to co-express four genes, the pRSFDuet-1 is loaded with L-amino acid oxidase genes and α-keto acid decarboxylase genes, and the pETDuet-1 is loaded with alcohol dehydrogenase genes and enzyme genes capable of reducing NAD(P).

After the co-expressed recombinant plasmids are obtained, the two plasmids are transformed into *Escherichia coli* B21, and positive transformants were obtained by screening with ampicillin and kanamycin plates so as to obtain the recombinant *Escherichia coli* strain.

4. Whole Cell Transformation of Phenylethanoids

Preparation of cells: According to the typical recombinant *Escherichia coli* culture and induced expression solution, the recombinant *Escherichia coli* strain is inoculated into an LB fermentation medium at a volume ratio of 2% (peptone 10 g/L, yeast powder 5 g/L, NaCl 10 g/L), when the cell $OD_{600}$ reaches 0.6-0.8, IPTG having a final concentration of 0.4 mM is added, and induced expression culture is carried out at 20° C. for 8 h. After the induced expression is completed, the cells are collected by centrifugation at 20° C. at 8000 rpm for 20 minutes.

The whole cell transformation system is as follows: the substrate concentration is controlled at 0.5-20 g/L according to the solubility of different substrates, the hydrogen donor having a concentration is 1-20 g/L is added according to the properties of the different constructed plasmids, the pH is adjusted to 4.0-8.0, and the amount of fresh wet cells is 10-200 g/L. The system is transformed at 15-40° C. for 0.5-48 hours. After the transformation is completed, the yield and optical activity are determined by liquid chromatography. When the constructed four enzyme co-expressed plasmid contains glucose dehydrogenase, the hydrogen donor is glucose. When the constructed four enzyme co-expressed plasmid contains formate dehydrogenase, the hydrogen donor is sodium formate. When the constructed four enzyme co-expressed plasmid contains phosphite dehydrogenase, the hydrogen donor is phosphorous acid.

The substrate in the whole cell transformation system is one of the following: L-phenylalanine, L-tyrosine, and L-dopa.

These substrates are subjected to corresponding whole cell transformation to correspondingly produce 2-phenylethanol, tyrosol and hydroxytyrosol.

5. Detection and Analysis of Samples

Quantitative analysis: A transformation solution is analyzed by PerkinElmer Series 200 high performance liquid chromatography. The chromatographic conditions are as follows: the mobile phase is methanol-0.1% formic acid water (40:60), a Hanbang Megres C18 chromatographic column (4.6×250 mm, 5 μm) is used, the flow rate is 1 ml/min, the column temperature is 30° C., the injection volume is 20 μL, and the detection wavelength is 210 nm.

In order to make the technical problems to be solved, technical solutions and advantageous effects of the present disclosure more clearly, the present disclosure will be described in detail below with reference to the embodiments. It should be noted that the specific embodiments described herein are merely illustrative of the present disclosure and are not intended to limit the present disclosure.

Example 1

Construction of Four Genes Co-Expressed System
(1) Primer Design
Primers for PCR amplification were designed.
(2) PCR Amplification According to the instructions for use provided by the manufacturer, genomic DNA of the strains in the logarithmic growth phase was extracted with Genomic DNA Purification Kit (Takara), and PCR amplification was carried out on the corresponding strains by using the primers in Table 1. The amplification system was as follows: PrimeSTAR HS DNA Polymerase (2.55 U/μL) 0.5 μL, 10×Prime STAR Buffer 10 μL, dNTP Mixture (2.5 mM each) 4 μL, template DNA 1 μL, Up primer (20 μM) 1 μL, Down primer (20 μM) 1 μL, ddH$_2$O replenished to 50 μL. The amplification procedure was: 94° C., 10 min; 94° C., 30 sec; 55° C., 30 sec; 72° C., 2 min, a total of 30 cycles; 72° C., 10 min. The PCR product was sent to The Beijing Genomics Institute for sequencing.

The L-amino acid oxidase genes pmaao and cmaao were cloned from *Proteus mirabilis* ATCC 29906 and *Cosenzaea myxofaciens* ATCC respectively; the α-keto acid decarboxylase genes pmkdc and llkdc were obtained from *Proteus mirabilis* ATCC 29906 and *Lactococcus lactis* ATCC 19435 respectively; the alcohol dehydrogenase genes ecadh1 and ecadh2 were obtained from *Escherichia coli* strain BL21; and the enzyme genes kpfdh, bsgdh, and papdh, which are capable of reducing NAD(P), were obtained from *Komaga-* taella phaffii ATCC 7627, *Bacillus subtilis* ATCC 13952 and *Pseudomonas abietaniphila* ATCC 70068 respectively.

(3) Construction of pRSFDuet-1 and pETDuet-1 Single Gene Plasmids

The pRSFDuet-1 and pETDuet-1 vector plasmids and the PCR products of cmaao, pmaao, ecadh1 and ecadh2 in step (2) were subjected to double digestion in a water bath at 37° C. for 1 h. The digestion system was: 10×cut buffer 5 μL, DNA 10 μL, restriction endonuclease SacI and restriction endonuclease HindIII each 1 μL, sterile water 33 μL.

Then, digested products were separately recovered and ligated in a water bath at 16° C. for 12 h-16 h, the pRSFDuet-1 was ligated with cmaao and pmaao respectively, and pETDuet-1 was ligated with ecadh1 and ecadh2 respectively. The ligation system was: 10×DNA ligase buffer 2.5 μL, DNA fragment 8 μL, vector DNA 2 μL, T4 DNA ligase 1 μL and sterile water 11.5 μL, totaling 25 μL.

Then, 100 μL of DH5α competent bacteria were added to the ligation system, slightly mixed uniformly, and subjected to ice-bath for 30 min. The system was placed in a preheated 42° C. water bath and stood for 90 s for heat shock treatment, and immediately subjected to ice-bath for 2 min. 1 mL of LB medium solution without antibiotics was added, and cultured at 37° C. for 1 h to resuscitate the cells. Finally, the cells formed by ligating the pRSFDuet-1 respectively with cmaao and pmaao were uniformly coated on a kanamycin-containing LB plate, the cells formed by ligating the pETDuet-1 respectively with ecadh1 and ecadh2 were uniformly coated on an ampicillin-containing LB plate, the single colony was cultured for 12 h, then the plasmid was extracted, and the correctness was verified by double digestion. Meanwhile, DNA sequencing was performed to ensure the accuracy. Finally, the correct transformants were preserved, and the following plasmids were obtained:

pRSFDuet-cmaao and pRSFDuet-pmaao containing L-amino acid oxidase genes; pETDuet-ecadh1 and pETDuet-ecadh2 containing alcohol dehydrogenase genes.

(4) Construction of L-Amino Acid Oxidase Gene/α-Keto Acid Decarboxylase Gene pRSFDuet-1 Co-Expressed Plasmids and Ethanol Dehydrogenase Gene/Enzyme Gene Capable of Reducing NAD(P) pETDuet-1 Co-Expressed Plasmids The digestion system was: 10×cut buffer 5 μL, DNA 10 μL, 1 μL of restriction endonuclease 1 and restriction endonuclease 2 each, and 33 μL of sterile water. The single gene plasmid constructed in step (3) and the PCR products of the pkmdc, Ilkdc, kpfdh, bsgdh and papdh in step (2) were subjected to double digestion in a water bath at 37° C. for 1 hour.

Due to the difference in the position of the restriction endonuclease of each gene, there are two cases as follows.

pRSFDuet-cmaao, pRSFDuet-pmaao, pmkdc and Ilkdc were subjected to double digestion with EcoR V and Kpn I.

pETDuet-ecadh1, pETDuet-ecadh2, kpfdh, bsgdh and papdh were subjected to double digestion with Bgl II and Xho I.

Then, digested products of the above two cases were separately recovered and ligated in a water bath at 16° C. for 12-16 hours. pRSFDuet-cmaao and pRSFDuet-pmaao were ligated with pmkdc and Ilkdc respectively, and pETDuet-ecadh1 and pETDuet-ecadh2 were ligated with kpfdh, bsgdh and papdh respectively. The ligation system was: 10×DNA ligase buffer 2.5 μL, DNA fragment 8 μL, vector DNA 2 μL, T4 DNA ligase 1 μL and sterile water 11.5 μL, totaling 25 μL.

Then, 100 μL of *E. coli* DH5a competent bacteria were added to the ligation system, slightly mixed uniformly, and subjected to ice-bath for 30 min. The system was placed in a preheated 42° C. water bath and stood for 90 s for heat shock treatment, and immediately subjected to ice-bath for 2 min. 1 mL of LB medium solution without antibiotics was added, and cultured at 37° C. for 1 h to resuscitate the cells. Finally, the cells formed by ligating the pRSFDuet-cmaao and pRSFDuet-pmaao respectively with pmkdc and Ilkdc were uniformly coated on a kanamycin-containing LB plate, the cells formed by ligating the pETDuet-ecadh1 and pETDuet-ecadh2 respectively with kpfdh, bsgdh and papdh were uniformly coated on an ampicillin-containing LB plate, the single colony was cultured for 12 hours, then the plasmid was extracted, and the correctness was verified by double digestion. Meanwhile, DNA sequencing was performed to ensure the accuracy. Finally, the correct transformants were preserved, and the following plasmids were obtained:

pRSFDuet-cmaao-pmkdc, pRSFDuet-cmaao-Ilkdc, pRSFDuet-pmaao-pmkdc and pRSFDuet-pmaao-Ilkdc containing L-amino acid oxidase genes and α-keto acid decarboxylase genes.

pETDuet-ecadh1-kpfdh, pETDuet-ecadh1-bsgdh, pETDuet-ecadh1-papdh, pETDuet-ecadh2-kpfdh, pETDuet-ecadh2-bsgdh and pETDuet-ecadh2-Papdh containing alcohol dehydrogenase genes and enzyme genes capable of reducing NAD(P).

(5) Construction of pRSFDuet-1 and pETDuet-1 Double Plasmid Four Genes Co-Expressed System According to the instructions for use provided by the manufacturer, pRSFDuet-cmaao-pmkdc, pRSFDuet-cmaao-Ilkdc, pRSFDuet-pmaao-pmkdc, pRSFDuet-pmaao-Ilkdc plasmid DNA1 and pETDuet-ecadh1-kpfdh, pETDuet-ecadh1-bsgdh, pETDuet-ecadh1-papdh, pETDuet-ecadh2-kpfdh, pETDuet-ecadh2-bsgdh, pETDuet-ecadh2-papdh plasmid DNA2 obtained in step (4) were extracted with TaKaRa MiniBEST Plasmid Purification Kit Ver. 4.0. Then, 1 μL of each of the above plasmid DNA1 and plasmid DNA2 was added to 100 μL of *E. coli* (BL21) competent bacteria, slightly mixed uniformly and subjected to ice-bath for 30 min. The system was placed in a preheated 42° C. water bath and stood for 90 s for heat shock treatment, and immediately subjected to ice-bath for 2 min. 1 mL of LB medium solution without antibiotics was added, and cultured at 37° C. for 1 hour to resuscitate the cells. Finally, the cells were uniformly coated on an LB plate containing ampicillin and kanamycin, the single colony was cultured for 12 hours, and then it was verified by PCR that four genes had been successfully transformed into *E. coli* (BL21). Meanwhile, DNA sequencing was performed to ensure the accuracy, and the strains were preserved for later use.

In the present Example, the following 8 engineered strains were finally constructed: *E. coli* BL21 (pRSFDuet-cmaao-pmkdc, pETDuet-bsgdh-ecadh1), *E. coli* BL21 (pRSFDuet-pmaao-Ilkdc, pETDuet-bsgdh-ecadh2), *E. coli* BL21 (pRSFDuet-cmaao-pmkdc, pETDuet-bsgdh-ecadh2), *E. coli* BL21 (pRSFDuet-pmaao-pmkdc, pETDuet-papdh-ecadh1), *E. coli* BL21 (pRSFDuet-pmaao-pmkdc, pETDuet-kpfdh-ecadh2), *E. coli* BL21 (pRSFDuet-cmaao-Ilkdc, pETDuet-bsgdh-ecadh1), *E. coli* BL21 (pRSFDuet-cmaao-Ilkdc, pETDuet-kpfdh-ecadh2), and *E. coli* BL21 (pRSFDuet-pmaao-Ilkdc, pETDuet-papdh-ecadh1), and the recombinant strains were numbered A, B, C, D, E, F, G and H respectively.

Example 2

Induced expression of the genetically engineered strain obtained in Example 1.

A single colony of the constructed genetically engineered strain was inoculated in 10 mL of LB medium (containing 0.1 g/L of ampicillin), incubated at 37° C. for 12 hours, inoculated by 2% in volume in an LB medium (a 1000 mL shake flask filled with 200 mL of liquid, containing 0.1 g/L of ampicillin), and cultured at 37° C. for 2.5 hours to the bacterial logarithmic growth phase ($OD_{600}$ reaches 0.6-0.8), IPTG was added until the concentration was 0.4 mM, and the system was cultured under the conditions of 20° C. and 200 rpm for 8 hours. After the induced expression was completed, the cells were collected by centrifugation at 20° C. at 8000 rpm for 20 minutes. According to the amount of cells required for transformation, the number of shake flasks can be increased to obtain sufficient cells.

Example 3

According to the induced expression method of Example 2, the cells of the recombinant strains numbered A, B, C, D, E, F, G and H obtained in Example 1 were collected after the induced expression was completed respectively. In a 100 mL reaction volume, the transformation condition of different substrates after being respectively mixed with whole cells was investigated. Under the conditions that the final concentration of the substrates was 0.5 g/L, the concentration of the glucose was 10 g/L, the pH was adjusted to 8.0, the added fresh whole cells weighed 20 g (wet weight) and the temperature was 30° C., the transformation was carried out for 24 hours, and the results were determined. The reaction conditions of various substrates are shown in the following table.

Wherein, the substrates are respectively L-phenylalanine, L-tyrosine and L-dopa, respectively corresponding to products 2-phenylethanol, tyrosol and hydroxytyrosol.

TABLE 2

Transformation condition of recombinant strains to different substrates

| Recombinant Strain | Yield of 2-Phenyl-ethanol (mg/L) | Yield of Tyrosol (mg/L) | Yield of Hydroxy-tyrosol (mg/L) |
| --- | --- | --- | --- |
| A | 468 | 444 | 341 |
| B | 371 | 301 | 161 |
| C | 401 | 292 | 220 |
| D | 455 | 336 | 310 |
| E | 432 | 467 | 240 |
| F | 324 | 297 | 190 |
| G | 329 | 246 | 162 |
| H | 370 | 288 | 183 |

Example 5

According to the induced expression method of Example 2, after the induced expression of the *E. coli* BL21 (pRSF-Duet-cmaao-pmkdc, pETDuet-bsgdh-ecadh2) obtained in Example 1 was completed, the cells were collected. In a 100 mL reaction volume, the concentration of L-phenylalanine was 20 g/L, the concentration of glucose was 20 g/L, the pH was adjusted to 8.0, the added fresh whole cells weighed 20 g (wet weight), and the temperature was 20° C., the transformation was carried out for 48 hours, and the results were tested. The 2-phenylethanol was produced, with the concentration being 18 g/L.

Example 6

According to the induced expression method of Example 2, after the induced expression of the *E. coli* BL21 (pRSF-Duet-pmaao-pmkdc, pETDuet-papdh-ecadh1) obtained in Example 1 was completed, the cells were collected. In a 100 mL reaction volume, wherein the concentration of L-dopa was 1 g/L, the concentration of phosphorous acid was 1 g/L, the pH was adjusted to 4.0, the added fresh whole cells weighed 10 g (wet weight), and the temperature was 35° C., the transformation was carried out for 0.5 hour, and the results were tested. The hydroxytyrosol was produced, with the concentration being 52 g/L.

Example 7

According to the induced expression method of Example 2, after the induced expression of the *E. coli* BL21 (pRSF-Duet-pmaao-pmkdc, pETDuet-kpfdh-ecadh2) obtained in Example 1 was completed, the cells were collected. In a 100 mL reaction volume, wherein the concentration of L-tyrosine was 0.5 g/L, the concentration of sodium formate was 20 g/L, the pH was adjusted to 6.0, the added fresh whole cells weighed 1 g (wet weight), and the temperature was 30° C., the transformation was carried out for 12 hours, and the results were tested. The tyrosol was produced, with the concentration being 104 mg/L.

Example 8

According to the induced expression method of Example 2, after the induced expression of the *E. coli* BL21 (pRSF-Duet-pmaao-pmkdc, pETDuet-kpfdh-ecadh2) obtained in Example 1 was completed, the cells were collected. In a 100 mL reaction volume, wherein the concentration of L-leucine was 0.5 g/L, the concentration of sodium formate was 1 g/L, the pH was adjusted to 7.0, the added fresh whole cells weighed 20 g (wet weight), and the temperature was 30° C., the transformation was carried out for 48 hours, and the results were tested. The isoamyl alcohol was produced, with the concentration being 320 mg/L.

Example 9

According to the induced expression method of Example 2, after the induced expression of the *E. coli* BL21 (pRSF-Duet-cmaao-llkdc, pETDuet-bsgdh-ecadh1) obtained in Example 1 was completed, the cells were collected. In a 100 mL reaction volume, wherein the concentration of L-phenylalanine was 0.5 g/L, the concentration of glucose was 1 g/L, the pH was adjusted to 8.0, the added fresh whole cells weighed 1 g (wet weight), and the temperature was 40° C., the transformation was carried out for 36 hours, and the results were tested. The 2-phenylethanol was produced, with the concentration being 155 mg/L.

Example 10

According to the induced expression method of Example 2, after the induced expression of the *E. coli* BL21 (pRSF-Duet-cmaao-llkdc, pETDuet-kpfdh-ecadh2) obtained in Example 1 was completed, the cells were collected. In a 100 mL reaction volume, wherein the concentration of L-tyrosine was 0.5 g/L, the concentration of sodium formate was 20 g/L, the pH was adjusted to 5.0, the added fresh whole cells weighed 1 5 g (wet weight), and the temperature was 30° C., the transformation was carried out for 48 hours, and the results were tested. The tyrosol was produced, with the concentration being 398 mg/L.

Example 11

According to the induced expression method of Example 2, after the induced expression of the *E. coli* BL21 (pRSF-Duet-pmaao-llkdc, pETDuet-papdh-ecadh1) obtained in Example 1 was completed, the cells were collected. In a 100 mL reaction volume, wherein the concentration of L-tyrosine was 0.5 g/L, the concentration of phosphorous acid was 5 g/L, the pH was adjusted to 7.0, the added fresh whole cells weighed 5 g (wet weight), and the temperature was 25° C., the transformation was carried out for 6 hours, and the results were tested. The tyrosol was produced, with the concentration being 210 mg/L.

What is claimed is:

1. A recombinant *Escherichia coli* strain, which is transformed with:
a polynucleotide encoding an L-amino acid oxidase enzyme and comprising the polynucleotide sequence of SEQ ID NO: 3 or SEQ ID NO: 4,
a polynucleotide encoding an α-keto acid decarboxylase enzyme and comprising the polynucleotide sequence of SEQ ID NO: 7 or SEQ ID NO: 8,
a polynucleotide encoding an alcohol dehydrogenase enzyme and comprising the polynucleotide sequence of SEQ ID NO: 11 or SEQ ID NO: 12, and
a polynucleotide encoding an enzyme capable of reducing NAD(P) to NAD(P)H, selected from: a formate dehydrogenase from *Komagataella* comprising the polynucleotide sequence of SEQ ID NO: 16, a glucose dehydrogenase from *Bacillus* comprising the polynucleotide sequence of SEQ ID NO: 17, or a phosphite dehydrogenase from *Pseudomonas* comprising the polynucleotide sequence of SEQ ID NO: 18,
wherein a combination of the four enzymes converts phenylalanine, tyrosine, and hydroxytyrosine into phenylethanol, tyrosol, and hydroxytyrosol, respectively, and
wherein the polynucleotides are on two different plasmids with one plasmid comprising the polynucleotides encoding the L-amino acid oxidase and α-keto acid decarboxylase enzymes, and another plasmid comprising the polynucleotide encoding the alcohol dehydrogenase enzyme and the enzyme capable of reducing NAD(P) to NAD(P)H.

2. A recombinant *Escherichia coli* strain, which is transformed with:
a polynucleotide encoding an L-amino acid oxidase enzyme and comprising the polynucleotide sequence of SEQ ID NO: 3 or SEQ ID NO: 4,
a polynucleotide encoding an α-keto acid decarboxylase enzyme and comprising the polynucleotide sequence of SEQ ID NO: 7 or SEQ ID NO: 8,
a polynucleotide encoding an alcohol dehydrogenase enzyme and comprising the polynucleotide sequence of SEQ ID NO: 11 or SEQ ID NO: 12, and
a polynucleotide encoding an enzyme capable of reducing NAD(P) to NAD(P)H, selected from: formate dehydrogenase from *Komagataella* and comprising the polynucleotide sequence of SEQ ID NO: 16, a glucose dehydrogenase from *Bacillus* and comprising the polynucleotide sequence of SEQ ID NO: 17, or a phosphite dehydrogenase from *Pseudomonas* comprising the polynucleotide sequence of SEQ ID NO: 18, wherein when expressed in the recombinant *Escherichia coli* strain, the four enzymes convert phenylalanine, tyrosine, and hydroxytyrosine into phenylethanol, tyrosol, and hydroxytyrosol, respectively, wherein the recombinant *Escherichia coli* strain co-expresses the polynucleotides of the four enzymes from plasmids pRSFDuet-1 and pETDuet-1, wherein the pRSFDuet-1 plasmid comprises the polynucleotides encoding the L-amino acid oxidase and the α-keto acid decarboxylase enzymes, and wherein the pETDuet-1 plasmid comprises the polynucleotides encoding the alcohol dehydrogenase enzyme and the enzyme capable of reducing NAD(P) to NAD(P)H.

3. The recombinant *Escherichia coli* strain according to claim 2, wherein the recombinant *Escherichia coli* strain is obtained by transforming a host *Escherichia coli* BL21 with the plasmids.

4. A method for producing a phenylethanoid selected from phenylethanol, tyrosol, or hydroxytyrosol, comprising culturing the recombinant *Escherichia coli* strain according to claim 1 under conditions suitable for producing the phenylthanoid.

5. The method according to claim 4, wherein the substrate for producing the phenylethanoid is any one or more of L-phenylalanine, L-tyrosine and L-dopa.

6. The method according to claim 4, wherein the production conditions comprise a fresh cell wet weight of 10-200 g/L, a substrate concentration of 0.5-20 g/L, a hydrogen donor concentration of 1-20 g/L, and a pH of 4.0-8.0; and the reaction is carried out at 15-40° C., for 0.5-48 hours.

7. The recombinant *Escherichia coli* strain according to claim 1, wherein cells of the recombinant *Escherichia coli* strain have been fermented and expression of the polynucleotides induced.

* * * * *

SEQUENCE LISTING

```
<160> NUMBER OF SEQ ID NOS: 18

<210> SEQ ID NO 1
<211> LENGTH: 471
<212> TYPE: PRT
<213> ORGANISM: Proteus mirabilis

<400> SEQUENCE: 1
```

| Met | Ala | Ile | Ser | Arg | Arg | Lys | Phe | Ile | Leu | Gly | Gly | Thr | Val | Val | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Val | Ala | Ala | Gly | Ala | Gly | Val | Leu | Thr | Pro | Met | Leu | Thr | Arg | Glu | Gly |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Arg | Phe | Val | Pro | Gly | Thr | Pro | Arg | His | Gly | Phe | Val | Glu | Gly | Thr | Gly |
|-----|-----|-----|-----|-----|-----|-----|-----|-----|-----|-----|-----|-----|-----|-----|-----|
|     |     |     | 35  |     |     |     | 40  |     |     |     |     | 45  |     |     |     |

| Gly | Pro | Leu | Pro | Lys | Gln | Asp | Asp | Val | Val | Ile | Gly | Ala | Gly | Ile |
|-----|-----|-----|-----|-----|-----|-----|-----|-----|-----|-----|-----|-----|-----|-----|
|     | 50  |     |     |     |     | 55  |     |     |     |     | 60  |     |     |     |

| Leu | Gly | Ile | Met | Thr | Ala | Ile | Asn | Leu | Ala | Glu | Arg | Gly | Leu | Ser | Val |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Thr | Ile | Val | Glu | Lys | Gly | Asn | Ile | Ala | Gly | Glu | Gln | Ser | Ser | Arg | Phe |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Tyr | Gly | Gln | Ala | Ile | Ser | Tyr | Lys | Met | Pro | Asp | Glu | Thr | Phe | Leu | Leu |
|-----|-----|-----|-----|-----|-----|-----|-----|-----|-----|-----|-----|-----|-----|-----|-----|
|     |     |     |     | 100 |     |     |     |     | 105 |     |     |     |     | 110 |     |

| His | His | Leu | Gly | Lys | His | Arg | Trp | Arg | Glu | Met | Asn | Ala | Lys | Val | Gly |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Ile | Asp | Thr | Thr | Tyr | Arg | Thr | Gln | Gly | Arg | Val | Glu | Val | Pro | Leu | Asp |
|-----|-----|-----|-----|-----|-----|-----|-----|-----|-----|-----|-----|-----|-----|-----|-----|
|     |     | 130 |     |     |     |     | 135 |     |     |     |     | 140 |     |     |     |

| Glu | Glu | Asp | Leu | Glu | Asn | Val | Arg | Lys | Trp | Ile | Asp | Ala | Lys | Ser | Lys |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Asp | Val | Gly | Ser | Asp | Ile | Pro | Phe | Arg | Thr | Lys | Met | Ile | Glu | Gly | Ala |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Glu | Leu | Lys | Gln | Arg | Leu | Arg | Gly | Ala | Thr | Thr | Asp | Trp | Lys | Ile | Ala |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Gly | Phe | Glu | Glu | Asp | Ser | Gly | Ser | Phe | Asp | Pro | Glu | Val | Ala | Thr | Phe |
|-----|-----|-----|-----|-----|-----|-----|-----|-----|-----|-----|-----|-----|-----|-----|-----|
|     |     |     | 195 |     |     |     |     | 200 |     |     |     |     | 205 |     |     |

| Val | Met | Ala | Glu | Tyr | Ala | Lys | Lys | Met | Gly | Ile | Lys | Ile | Phe | Thr | Asn |
|-----|-----|-----|-----|-----|-----|-----|-----|-----|-----|-----|-----|-----|-----|-----|-----|
|     |     | 210 |     |     |     |     | 215 |     |     |     |     | 220 |     |     |     |

| Cys | Ala | Ala | Arg | Gly | Leu | Glu | Thr | Gln | Ala | Gly | Val | Ile | Ser | Asp | Val |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Val | Thr | Glu | Lys | Gly | Pro | Ile | Lys | Thr | Ser | Arg | Val | Val | Ala | Gly |
|-----|-----|-----|-----|-----|-----|-----|-----|-----|-----|-----|-----|-----|-----|-----|
|     |     |     |     | 245 |     |     |     |     | 250 |     |     |     |     | 255 |

| Gly | Val | Trp | Ser | Arg | Leu | Phe | Met | Gln | Asn | Leu | Asn | Val | Asp | Val | Pro |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Thr | Leu | Pro | Ala | Tyr | Gln | Ser | Gln | Gln | Leu | Ile | Ser | Ala | Ala | Pro | Asn |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Ala | Pro | Gly | Gly | Asn | Val | Ala | Leu | Pro | Gly | Gly | Ile | Phe | Phe | Arg | Glu |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Gln | Ala | Asp | Gly | Thr | Tyr | Ala | Thr | Ser | Pro | Arg | Val | Ile | Val | Ala | Pro |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Val | Val | Lys | Glu | Ser | Phe | Thr | Tyr | Gly | Tyr | Lys | Tyr | Leu | Pro | Leu | Leu |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

```
Ala Leu Pro Asp Phe Pro Val His Ile Ser Leu Asn Glu Gln Leu Ile
            340                 345                 350

Asn Ser Phe Met Gln Ser Thr His Trp Asp Leu Asn Glu Glu Ser Pro
        355                 360                 365

Phe Glu Lys Tyr Arg Asp Met Thr Ala Leu Pro Asp Leu Pro Glu Leu
    370                 375                 380

Asn Ala Ser Leu Glu Lys Leu Lys Lys Glu Phe Pro Ala Phe Lys Glu
385                 390                 395                 400

Ser Thr Leu Ile Asp Gln Trp Ser Gly Ala Met Ala Ile Ala Pro Asp
                405                 410                 415

Glu Asn Pro Ile Ile Ser Asp Val Lys Glu Tyr Pro Gly Leu Val Ile
            420                 425                 430

Asn Thr Ala Thr Gly Trp Gly Met Thr Glu Ser Pro Val Ser Ala Glu
        435                 440                 445

Ile Thr Ala Asp Leu Leu Gly Lys Lys Pro Val Leu Asp Ala Lys
    450                 455                 460

Pro Phe Ser Leu Tyr Arg Phe
465                 470

<210> SEQ ID NO 2
<211> LENGTH: 466
<212> TYPE: PRT
<213> ORGANISM: Cosenzaea myxofaciens

<400> SEQUENCE: 2

Met Leu Gly Ile Gly Ala Ala Gly Val Leu Ala Gly Gly Ala Ala Thr
1               5                   10                  15

Leu Val Pro Met Val Arg Arg Asp Gly Lys Phe Val Glu Ser Lys Ser
            20                  25                  30

Arg Ala Leu Phe Val Glu Ser Thr Glu Gly Ala Leu Pro Ser Glu Ser
        35                  40                  45

Asp Val Val Ile Ile Gly Gly Gly Ile Gln Gly Ile Met Thr Ala Ile
    50                  55                  60

Asn Leu Ala Glu Arg Gly Met Ser Val Thr Ile Leu Glu Lys Gly Glu
65                  70                  75                  80

Val Ala Gly Glu Gln Ser Gly Arg Ala Tyr Ser Gln Ile Ile Ser Tyr
                85                  90                  95

Gln Thr Ser Pro Glu Ile Phe Pro Leu His His Tyr Gly Lys Ile Leu
            100                 105                 110

Trp Arg Gly Met Asn Glu Lys Ile Gly Ala Asp Thr Ser Tyr Arg Thr
        115                 120                 125

Gln Gly Arg Val Glu Ala Leu Ala Asp Glu Lys Ala Leu Asp Arg Ala
    130                 135                 140

Gln Glu Trp Ile Lys Thr Ala Lys Glu Thr Ala Gly Phe Asp Val Pro
145                 150                 155                 160

Leu Asn Thr Arg Ile Ile Lys Gly Glu Glu Leu Ser Asn Arg Leu Val
                165                 170                 175

Gly Ala Gln Thr Pro Trp Thr Val Ala Ala Phe Glu Glu Asp Ser Gly
            180                 185                 190

Ser Val Asp Pro Glu Thr Gly Thr Pro Thr Leu Ala Arg Tyr Ala Lys
        195                 200                 205

Gln Ile Gly Val Lys Ile Tyr Thr His Cys Ala Val Arg Gly Ile Glu
    210                 215                 220

Thr Ala Gly Gly Lys Ile Ser Asp Val Val Thr Glu Lys Gly Ala Ile
225                 230                 235                 240
```

```
Arg Thr Ser Asn Val Val Leu Ala Gly Gly Ile Trp Ser Arg Leu Phe
            245                 250                 255

Met Gly Asn Met Gly Val Asp Leu Pro Thr Leu Asn Val Tyr Leu Ser
            260                 265                 270

Gln Gln Arg Val Ser Gly Val Pro Gly Ala Pro Arg Gly Asn Val His
            275                 280                 285

Leu Pro Asn Gly Ile His Phe Arg Glu Gln Ala Asp Gly Thr Tyr Ala
            290                 295                 300

Val Ala Pro Arg Ile Phe Thr Ser Ser Ile Val Lys Asp Ser Phe Leu
305                 310                 315                 320

Leu Gly Pro Lys Phe Met His Leu Leu Gly Gly Gly Glu Leu Pro Leu
            325                 330                 335

Glu Phe Ser Ile Gly Glu Asp Leu Phe Asn Ser Phe Lys Met Pro Thr
            340                 345                 350

Ser Trp Lys Leu Asp Glu Lys Ser Pro Phe Glu Gln Tyr Arg Ile Ala
            355                 360                 365

Thr Ala Thr Gln Asn Thr Glu His Leu Asp Ala Val Phe Gln Arg Met
370                 375                 380

Lys Thr Glu Phe Pro Val Phe Glu Lys Ser Gln Ile Val Glu Arg Trp
385                 390                 395                 400

Gly Ala Val Val Ser Pro Thr Phe Asp Glu Leu Pro Ile Ile Ser Glu
            405                 410                 415

Val Lys Glu Tyr Pro Gly Leu Val Ile Asn Thr Ala Thr Val Trp Gly
            420                 425                 430

Met Thr Glu Gly Pro Ala Ala Gly Glu Val Thr Ala Asp Ile Val Thr
            435                 440                 445

Gly Lys Lys Pro Val Ile Asp Pro Thr Pro Phe Ser Leu Asp Arg Phe
450                 455                 460

Lys Ser
465

<210> SEQ ID NO 3
<211> LENGTH: 1413
<212> TYPE: DNA
<213> ORGANISM: Proteus mirabilis

<400> SEQUENCE: 3
atggcaataa gtagaagaaa atttattctt ggtggcacag tggttgctgt tgctgcaggc      60 gctgggggttt taacacctat gttaacgcga aagggcgtt ttgttcctgg tacgccgaga     120
catggttttg ttgagggaac tggcggtcca ttaccgaaac aagatgatgt tgttgtaatt     180
ggtgcgggta ttttaggtat catgaccgcg attaaccttg ctgagcgtgg cttatctgtc     240
acaatcgttg aaaaaggaaa tattgccggc gaacaatcat ctcgattcta tggtcaagct     300
attagctata aaatgccaga tgaaaccttc ttattacatc acctcgggaa gcaccgctgg     360
cgtgagatga acgctaaagt tggtattgat accacttatc gtacacaagg tcgtgtagaa     420
gttcctttag atgaagaaga tttagaaaac gtaagaaaat ggattgatgc taaaagcaaa     480
gatgttggct cagacattcc atttagaaca aaaatgattg aaggcgctga gttaaaacag     540
cgtttacgtg gcgctaccac tgattggaaa attgctggtt cgaagaaga ctcaggaagt     600 ttcgatcctg aagttgcgac ttttgtgatg cagaatatg ccaaaaaaat gggtatcaaa     660
attttcacaa actgtgcagc ccgtggttta gaaacgcaag ctggtgttat ttctgatgtt     720
gtaacagaaa aaggaccaat taaaacctct cgtgttgttg tcgccggtgg tgtttggtca     780
```

```
cgtttatttta tgcagaacct aaatgttgat gtaccaacat tacctgctta tcaatcacag      840
caattaatta gcgcagcacc aaatgcgcca ggtggaaacg ttgctttacc cggcggaatt      900
ttctttcgtg aacaagcgga tggaacgtat gcaacttctc ctcgtgtcat tgttgctccg      960
gtagtaaaag aatcatttac ttacggctat aaatatttac ctctgctggc tttacctgat     1020
ttcccagtac atatttcgtt aaatgagcag ttgattaatt cctttatgca atcaacacat     1080
tgggatctta atgaagagtc gccatttgaa aaatatcgtg atatgaccgc tctgcctgat     1140
ctgccagaat taaatgcctc actggaaaaa ctgaaaaaag agttcccagc atttaaagaa     1200
tcaacgttaa ttgatcagtg gagtggtgcg atggcgattg caccagatga aaacccaatt     1260
atctctgatg ttaaagagta tccaggtcta gttattaata ctgcaacagg ttggggaatg     1320
actgaaagcc ctgtatcagc agaaattaca gcagatttat tattaggcaa aaaaccagta     1380
ttagatgcca aaccatttag tctgtatcgt ttc                                   1413

<210> SEQ ID NO 4
<211> LENGTH: 1398
<212> TYPE: DNA
<213> ORGANISM: Cosenzaea myxofaciens

<400> SEQUENCE: 4
atgctaggca ttggtgctgc tggcgtactt gctggtggtg cggccacttt agttccaatg        60
gttcgccgtg atggtaaatt tgttgaatct aaatcaagag ctttatttgt tgaaagtact       120
gagggtgccc tgccatcaga atctgatgtg gtcattattg gaggtggtat tcaaggtatc       180
atgacagcga ttaatttagc tgaacgtggt atgagtgtca ccatttttaga aaaaggcgag       240 gttgctggag agcaatcagg ccgcgcatac agccaaatca ttagctacca aacgtcaccc       300
gaaattttcc cattgcatca ttacggaaaa attttatggc gtggtatgaa cgaaaaaatt       360
ggtgctgata ccagctatcg cacacaaggt cgagttgaag cgcttgctga tgaaaaagca       420
ttagatagag cgcaagaatg gatcaaaaca gccaagaaa cagcaggatt tgatgtacct       480
ttaaatactc gtattattaa gggtgaagag ttatcaaata gattagtagg tgcacaaaca       540
ccttggactg ttgctgcttt tgaagaagat tctggttctg tcgatcctga aacgggtaca       600
ccaacattag cgcgttatgc taaacaaatt ggtgttaaaa tctatactca ttgcgcagta       660
agaggtattg aaacagcagg tggtaaaatt tctgatgttg tcactgaaaa aggtgcaata       720
agaacatcta acgttgttct tgctgggggt atttggtcac gtttattcat ggggaatatg       780
ggggttgatc ttccaacctt gaatgtttac ttatcacaac aacgtgtatc cggtgttcca       840
ggcgcaccac gtggtaatgt gcatttacca aatggtatcc actttcgaga caagctgac       900 ggcacttatg ctgtagcccc acgtatcttc acaagctcca ttgttaaaga tagttttccta      960 ttagggccta aatttatgca cttattaggt ggtggtgagc taccattaga attctctatt     1020
ggtgaagact tgtttaattc attcaaaatg cctacatcat ggaaattaga cgaaaaatca     1080
ccttttgagc aatatcgcat cgcgactgca acacaaaata ctgagcattt agatgctgta     1140
ttccaaagaa tgaaaacaga attcccagta tttgaaaaat cacaaattgt tgaacgttgg     1200
ggtgcagttg taagtccaac atttgatgaa ttaccgatta tttcagaagt aaaagagtac     1260
ccaggtcttg ttatcaatac agcgacagtg tggggaatga cagaaggtcc tgctgccggt     1320
gaagttaccg cagatattgt gacgggtaaa aaacccgtca ttgatccaac gccatttagt     1380
ttggatcgct ttaagtcg                                                   1398
```

<210> SEQ ID NO 5
<211> LENGTH: 549
<212> TYPE: PRT
<213> ORGANISM: Proteus mirabilis

<400> SEQUENCE: 5

Met Thr Asn Thr Val Ile Lys Tyr Val Leu Asp Arg Leu Tyr Asp Leu
1               5                   10                  15

Gly Ile Lys Asp Ile Phe Gly Val Ala Gly Asp Tyr Ala Phe Pro Ile
            20                  25                  30

Glu Asp Thr Val Cys Asn Asn Gln Gln Gln Arg Trp Ile Gly Asn Cys
        35                  40                  45

Asn Glu Leu Asn Ala Ala Tyr Ala Ala Asp Gly Tyr Ala Arg Ile Lys
    50                  55                  60

Gly Met Ala Ala Leu Ser Thr Thr Phe Gly Val Gly Glu Leu Ser Ala
65                  70                  75                  80

Ile Asn Ala Ile Ala Gly Ala Tyr Ala Glu Asn Leu Pro Ile Phe His
                85                  90                  95

Leu Val Gly Met Pro Ala Ser Gly Val Gln Lys Ser Lys Arg Leu Val
            100                 105                 110

His His Thr Leu Gly Asn Gly Asp Phe Asp Val Phe Tyr Gln Ile Ala
        115                 120                 125

Gln Arg Leu Ala Cys Ala His Thr Ile Leu Thr Pro Glu Asn Cys Val
    130                 135                 140

Glu Glu Met Glu Arg Val Ile Glu Ala Ala Leu Lys Glu Arg Arg Pro
145                 150                 155                 160

Val Tyr Ile Gly Ile Pro Ser Asp Tyr Ala Asn Ser Gln Val Val Ala
                165                 170                 175

Pro Leu Ser Val Thr Ala Pro Gln Lys Pro Thr Ser Asp Lys Ala Thr
            180                 185                 190

Leu Glu Lys Ala Val Ser Ala Ile Ile Glu Lys Leu Thr His Ser Asn
        195                 200                 205

Asn Val Cys Val Leu Pro Gly Phe Leu Ser Ala Arg Leu Gly Leu Thr
    210                 215                 220

Asp Lys Ile Gln His Phe Ile Asp Lys Thr Gly Leu Pro Tyr Ala Thr
225                 230                 235                 240

Met Phe Met Asp Lys Ser Ile Leu Ser Glu Ser Asn Ala Gln Tyr Val
                245                 250                 255

Gly Met Tyr Asp Gly Gln Leu Met Thr Pro Glu Val Arg Glu Phe Val
            260                 265                 270

Glu Ser Ser Glu Tyr Ile Leu Gly Ile Gly Thr Leu Met Thr Asp Phe
        275                 280                 285

Asn Thr Gly Ser Phe Thr Ala Asn Ile Lys Ser Glu Gln Leu Ile Ser
    290                 295                 300

Ile Met Pro Asp Tyr Val Glu Ile Asp Ser Val Ile Tyr Ser Cys Val
305                 310                 315                 320

Tyr Met Thr Asp Ile Leu Ser Glu Leu Thr Gln Arg Leu Pro Asn Lys
                325                 330                 335

Thr Tyr His Lys Ile Thr Ala Lys Gly Leu Gly Glu Ala Val Ile Ser
            340                 345                 350

Asp Asn Asp Lys Ile Thr Ala Gln Tyr Leu Tyr Pro Arg Leu Glu Gln
        355                 360                 365

Phe Phe Lys Pro Asn Asp Ile Ile Ile Ala Glu Thr Gly Thr Ser Ser
    370                 375                 380

Met Gly Leu Gly Phe Ala Leu Leu Pro Glu Gly Ala Gln Phe His Asn
385                 390                 395                 400

Gln Thr Leu Trp Gly Ser Ile Gly Trp Ala Thr Pro Ala Ala Leu Gly
            405                 410                 415

Ala Ala Leu Ala Ala Pro Glu Lys Arg Ile Ile Leu Ile Thr Gly Glu
420                 425                 430

Gly Ser His Gln Leu Thr Val Gln Glu Ile Ser Gln Phe Val Arg Phe
            435                 440                 445

Gly Leu Lys Pro Ile Ile Leu Val Leu Asn Asn Asp Gly Tyr Leu Ile
        450                 455                 460

Glu Arg Leu Leu Cys Asp Tyr Pro Glu Ala Tyr Tyr Asn Asp Leu Ala
465                 470                 475                 480

Gln Trp Asn Tyr His Gln Leu Pro Gln Ala Phe Gly Ala Thr Asp Trp
                485                 490                 495

Tyr Ser Glu Lys Val Thr Thr Ala Ser Gly Leu Asp Asn Ala Leu Asn
            500                 505                 510

Lys Ala Ala Leu Thr Asn Ser Ala Ser Tyr Ile Glu Ile Val Thr Glu
        515                 520                 525

Arg Tyr Glu Ala Ser Glu Leu Ala Gln Lys Leu Lys Glu Ser Lys Ser
        530                 535                 540

Ser Leu Tyr Ser Phe
545

<210> SEQ ID NO 6
<211> LENGTH: 548
<212> TYPE: PRT
<213> ORGANISM: Lactococcus lactis

<400> SEQUENCE: 6

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro

```
              195                 200                 205
Ile Val Ile Thr Gly His Glu Ile Ser Phe Gly Leu Glu Lys Thr
            210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
            290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
            515                 520                 525

Glu Asp Ala Pro Lys Val Leu Lys Lys Met Gly Lys Leu Phe Ala Glu
            530                 535                 540

Gln Asn Lys Ser
545

<210> SEQ ID NO 7
<211> LENGTH: 1647
<212> TYPE: DNA
<213> ORGANISM: Proteus mirabilis

<400> SEQUENCE: 7
atgacaaaca cagttattaa gtacgtttta gaccgattat atgatttagg tatcaaagat      60 attttggtg ttgctggtga ttacgccttc cctattgaag acactgtttg caacaaccaa     120
```

```
caacaacgtt ggattggtaa ctgtaatgaa ttaaatgcgg catatgctgc agatggctat      180
gcccgaatta aaggtatggc agcattatcc actacctttg gcgtaggtga attaagtgcg      240
attaacgcta ttgctggtgc ctatgctgaa aatttaccga ttttccattt agttggcatg      300
ccagcaagtg gcgtacaaaa aagtaaacgc cttgtgcatc atactttagg taatggtgat      360
tttgatgttt tttatcagat tgctcagcgc cttgcttgcg ctcatactat tttaacaccc      420
gaaaattgtg tggaagaaat ggagcgcgta atagaagcag cattaaaaga gcgtcgtcct      480
gtttatattg gtataccttc agattatgct aatagccaag tagtagcgcc gttatctgtt      540
accgcaccac aaaagccaac aagtgataaa gcaacattag aaaaagcagt atcagcaatc      600
attgagaaac tcacccacag caataatgtc tgtgtattac caggcttttt atctgcacgt      660
ttagggttaa cagataaaat ccagcatttt attgataaaa caggtttacc ttatgccact      720
atgtttatgg ataaaagcat attaagtgaa tctaacgcgc aatatgttgg tatgtatgac      780
ggacaattaa tgacaccaga ggtcagagaa tttgtcgaaa gtagtgaata tatattaggg      840
atcggtacat taatgactga ctttaataca ggcagcttca ctgctaatat taaatcagaa      900
caattaatca gtattatgcc agattatgtt gaaattgatt ctgtgatcta ctcctgcgtt      960
tatatgacag atattctttc tgaattaacc caacgactac caaataaaac ttatcataaa     1020
ataacagcga aaggattagg tgaagcggtt atatctgata atgataaaat tacagcacaa     1080
tatctctatc ctcgtttaga acaattcttt aaacctaatg atattattat tgcagaaaca     1140
ggaacctcat ccatgggatt aggcttcgct ttattacctg aaggtgcaca atttcataat     1200
caaacactat ggggctctat tggttgggca acaccggctg cattaggcgc tgcgttagcg     1260
gcaccagaaa aacgcattat tttaattacc ggtgaaggct ctcatcaatt aacagtacaa     1320
gaaattagtc aatttgttcg tttcggttta aaacctatta ttctagtatt aaataacgat     1380
ggttatttaa tagagagatt attatgtgat taccccgaag cttattataa tgatttagct     1440
cagtggaact atcatcagtt accgcaagcc tttggtgcaa cagattggta tagtgaaaaa     1500
gtaactacag caagtggact agataatgcg ttaaataaag ccgcactaac aaatagcgca     1560
tcttatattg agatagtcac agagcgatat gaggcctctg aattagcgca aaaattaaaa     1620
gaatcaaaaa gttcattata ttcattc                                        1647
```

<210> SEQ ID NO 8
<211> LENGTH: 1644
<212> TYPE: DNA
<213> ORGANISM: Lactococcus lactis

<400> SEQUENCE: 8

```
atgtatacag taggagatta cctattagac cgattacacg agttaggaat tgaagaaatt       60
tttggagtcc ctggagacta taacttacaa ttttttagatc aaattatttc ccgcaaggat      120
atgaaatggg tcggaaatgc taatgaatta aatgcttcat atatggctga tggctatgct      180
cgtactaaaa aagctgccgc atttcttaca acctttggag taggtgaatt gagtgcagtt      240
aatggattag caggaagtta cgccgaaaat ttaccagtag tagaaatagt gggatcacct      300
acatcaaaag ttcaaaatga aggaaaattt gttcatcata cgctggctga cggtgatttt      360
aaacacttta tgaaaatgca cgaacctgtt acagcagctc gaactttact gacagcagaa      420
aatgcaaccg ttgaaattga ccgagtactt tctgcactat aaaagaaag aaaacctgtc      480 tatatcaact taccagttga tgttgctgct gcaaaagcag agaaaccctc actccctttg      540
```

```
aaaaaagaaa actcaacttc aaatacaagt gaccaagaga tcttgaacaa aattcaagaa    600
agcttgaaaa atgccaaaaa accaatcgtg attacaggac atgaaataat tagttttggc    660
ttagaaaaaa cagtctctca atttatttca aagacaaaac tacctattac gacattaaac    720
tttggaaaaa gttcagttga tgaagctctc ccttcatttt taggaatcta taatggtaaa    780
ctctcagagc ctaatcttaa agaattcgtg gaatcagccg acttcatcct gatgcttgga    840
gttaaactca cagactcttc aacaggagcc ttcactcatc atttaaatga aaataaaatg    900
atttcactga atatagatga aggaaaaata tttaacgaaa gcatccaaaa ttttgatttt    960
gaatccctca tctcctctct cttagaccta agcgaaatag aatacaaagg aaaatatatc   1020
gataaaaagc aagaagactt tgttccatca aatgcgcttt tatcacaaga ccgcctatgg   1080
caagcagttg aaaacctaac tcaaagcaat gaaacaatcg ttgctgaaca agggacatca   1140
ttctttggcg cttcatcaat tttcttaaaa ccaaagagtc attttattgg tcaaccctta   1200
tggggatcaa ttggatatac attcccagca gcattaggaa gccaaattgc agataaagaa   1260
agcagacacc ttttatttat tggtgatggt tcacttcaac ttacggtgca agaattagga   1320
ttagcaatca gagaaaaaat taatccaatt tgctttatta tcaataatga tggttataca   1380
gtcgaaagag aaattcatgg accaaatcaa agctacaatg atattccaat gtggaattac   1440
tcaaaattac cagaatcatt tggagcaaca gaagaacgag tagtctcgaa atcgttaga    1500 actgaaaatg aatttgtgtc tgtcatgaaa gaagctcaag cagatccaaa tagaatgtac   1560
tggattgagt taattttggc aaaagaagat gcaccaaaag tactgaaaaa aatgggcaaa   1620
ctatttgctg aacaaaataa atca                                          1644

<210> SEQ ID NO 9
<211> LENGTH: 339
<212> TYPE: PRT
<213> ORGANISM: Escherichia coli

<400> SEQUENCE: 9

Met Ser Met Ile Lys Ser Tyr Ala Ala Lys Glu Ala Gly Gly Glu Leu
1               5                   10                  15

Glu Val Tyr Glu Tyr Asp Pro Gly Glu Leu Arg Pro Gln Asp Val Glu
            20                  25                  30

Val Gln Val Asp Tyr Cys Gly Ile Cys His Ser Asp Leu Ser Met Ile
        35                  40                  45

Asp Asn Glu Trp Gly Phe Ser Gln Tyr Pro Leu Val Ala Gly His Glu
    50                  55                  60

Val Ile Gly Arg Val Val Ala Leu Gly Ser Ala Gln Asp Lys Gly
65                  70                  75                  80

Leu Gln Val Gly Gln Arg Val Gly Ile Gly Trp Thr Ala Arg Ser Cys
                85                  90                  95

Gly His Cys Asp Ala Cys Ile Ser Gly Asn Gln Ile Asn Cys Glu Gln
            100                 105                 110

Gly Ala Val Pro Thr Ile Met Asn Arg Gly Gly Phe Ala Glu Lys Leu
        115                 120                 125

Arg Ala Asp Trp Gln Trp Val Ile Pro Leu Pro Glu Asn Ile Asp Ile
    130                 135                 140

Glu Ser Ala Gly Pro Leu Leu Cys Gly Gly Ile Thr Val Phe Lys Pro
145                 150                 155                 160

Leu Leu Met His His Ile Thr Ala Thr Ser Arg Val Gly Val Ile Gly
                165                 170                 175
```

```
Ile Gly Gly Leu Gly His Ile Ala Ile Lys Leu Leu His Ala Met Gly
                180                 185                 190

Cys Glu Val Thr Ala Phe Ser Ser Asn Pro Ala Lys Glu Gln Glu Val
            195                 200                 205

Leu Ala Met Gly Ala Asp Lys Val Val Asn Ser Arg Asp Pro Gln Ala
        210                 215                 220

Leu Lys Ala Leu Ala Gly Gln Phe Asp Leu Ile Ile Asn Thr Val Asn
225                 230                 235                 240

Val Ser Leu Asp Trp Gln Pro Tyr Phe Glu Ala Leu Thr Tyr Gly Gly
                245                 250                 255

Asn Phe His Thr Val Gly Ala Val Leu Thr Pro Leu Ser Val Pro Ala
            260                 265                 270

Phe Thr Leu Ile Ala Gly Asp Arg Ser Val Ser Gly Ser Ala Thr Gly
        275                 280                 285

Thr Pro Tyr Glu Leu Arg Lys Leu Met Arg Phe Ala Ala Arg Ser Lys
290                 295                 300

Val Ala Pro Thr Thr Glu Leu Phe Pro Met Ser Lys Ile Asn Asp Ala
305                 310                 315                 320

Ile Gln His Val Arg Asp Gly Lys Ala Arg Tyr Arg Val Val Leu Lys
                325                 330                 335

Ala Asp Tyr

<210> SEQ ID NO 10
<211> LENGTH: 349
<212> TYPE: PRT
<213> ORGANISM: Escherichia coli

<400> SEQUENCE: 10

Met Lys Ile Lys Ala Val Gly Ala Tyr Ser Ala Lys Gln Pro Leu Glu
1               5                   10                  15

Pro Met Asp Ile Thr Arg Arg Glu Pro Gly Pro Asn Asp Val Lys Ile
            20                  25                  30

Glu Ile Ala Tyr Cys Gly Val Cys His Ser Asp Leu His Gln Val Arg
        35                  40                  45

Ser Glu Trp Ala Gly Thr Val Tyr Pro Cys Val Pro Gly His Glu Ile
    50                  55                  60

Val Gly Arg Val Val Ala Val Gly Asp Gln Val Glu Lys Tyr Ala Pro
65                  70                  75                  80

Gly Asp Leu Val Gly Val Gly Cys Ile Val Asp Ser Cys Lys His Cys
                85                  90                  95

Glu Glu Cys Glu Asp Gly Leu Glu Asn Tyr Cys Asp His Met Thr Gly
            100                 105                 110

Thr Tyr Asn Ser Pro Thr Pro Asp Glu Pro Gly His Thr Leu Gly Gly
        115                 120                 125

Tyr Ser Gln Gln Ile Val Val His Glu Arg Tyr Val Leu Arg Ile Arg
    130                 135                 140

His Pro Gln Glu Gln Leu Ala Ala Val Ala Pro Leu Leu Cys Ala Gly
145                 150                 155                 160

Ile Thr Thr Tyr Ser Pro Leu Arg His Trp Gln Ala Gly Pro Gly Lys
                165                 170                 175

Lys Val Gly Val Val Gly Ile Gly Gly Leu Gly His Met Gly Ile Lys
            180                 185                 190

Leu Ala His Ala Met Gly Ala His Val Val Ala Phe Thr Thr Ser Glu
        195                 200                 205
```

```
Ala Lys Arg Glu Ala Ala Lys Ala Leu Gly Ala Asp Glu Val Val Asn
        210                 215                 220
Ser Arg Asn Ala Asp Glu Met Ala Ala His Leu Lys Ser Phe Asp Phe
225                 230                 235                 240
Ile Leu Asn Thr Val Ala Ala Pro His Asn Leu Asp Asp Phe Thr Thr
                245                 250                 255
Leu Leu Lys Arg Asp Gly Thr Met Thr Leu Val Gly Ala Pro Ala Thr
            260                 265                 270
Pro His Lys Ser Pro Glu Val Phe Asn Leu Ile Met Lys Arg Arg Ala
        275                 280                 285
Ile Ala Gly Ser Met Ile Gly Gly Ile Pro Thr Gln Glu Met Leu
290                 295                 300
Asp Phe Cys Ala Glu His Gly Ile Val Ala Asp Ile Glu Met Ile Arg
305                 310                 315                 320
Ala Asp Gln Ile Asn Glu Ala Tyr Glu Arg Met Leu Arg Gly Asp Val
                325                 330                 335
Lys Tyr Arg Phe Val Ile Asp Asn Arg Thr Leu Thr Asp
            340                 345

<210> SEQ ID NO 11
<211> LENGTH: 1017
<212> TYPE: DNA
<213> ORGANISM: Escherichia coli

<400> SEQUENCE: 11
atgtcgatga taaaaagcta tgccgcaaaa gaagcgggcg gagaactgga agtttatgag       60
tacgatcccg gtgagctgag gccacaagat gttgaagtgc aggtggatta ctgcgggatc      120
tgccattccg atctgtcgat gatcgataac gaatggggat tttcacaata tccgctggtt      180
gccgggcatg aggtgattgg gcgcgtggtg gcactcggga gcgccgcgca ggataaaggt      240
ttgcaggtcg gtcagcgtgt cgggattggc tggacggcgc gtagctgtgg tcactgcgac      300
gcctgtatta gcggtaatca gatcaactgc gagcaaggtg cggtgccgac gattatgaat      360
cgcggtggct tgccgagaa gttgcgtgcg gactggcaat gggtgattcc actgccagaa      420
aatattgata tcgagtccgc cggggccgctg ttgtgcggcg gtatcacggt ctttaaacca      480
ctgttgatgc accatatcac tgctaccagc cgcgttgggg taattggtat tggcgggctg      540
gggcatatcg ctataaaact tctgcacgca atgggatgcg aggtgacagc ctttagttct      600
aatccggcga aagagcagga agtgctggcg atgggtgccg ataaagtggt gaatagccgc      660
gatccgcagg cactgaaagc actggcgggg cagtttgatc tcattatcaa caccgtcaac      720
gtcagcctcg actggcagcc ctattttgag gcgctgacct atggcggtaa tttccatacg      780
gtcggtgcgg ttctcacgcc gctgtctgtt ccggccttta cgttaattgc gggcgatcgc      840
agcgtctctg gttctgctac cggcacgcct tatgagctgc gtaagctgat gcgttttgcc      900
gcccgcagca aggttgcgcc gaccaccgaa ctgttcccga tgtcgaaaat taacgacgcc      960
atccagcatg tgcgcgacgg taaggcgcgt taccgcgtgg tgttgaaagc cgattat       1017

<210> SEQ ID NO 12
<211> LENGTH: 1047
<212> TYPE: DNA
<213> ORGANISM: Escherichia coli

<400> SEQUENCE: 12
atgaagatca aagctgttgg tgcatattcc gctaaacaac cacttgaacc gatggatatc       60
```

```
acccggcgtg aaccgggacc gaatgatgtc aaaatcgaaa tcgcttactg tggcgtttgc    120
cattccgatc tccaccaggt ccgttccgag tgggcgggga cggtttaccc ctgcgtgccg    180
ggtcatgaaa ttgtggggcg tgtggtagcc gttggtgatc aggtagaaaa atatgcgccg    240
ggcgatctgg tcggtgtcgg ctgcattgtc gacagttgta acattgcga agagtgtgaa    300
gacgggttgg aaaactactg tgatcacatg accggcacct ataactcgcc gacgccggac    360
gaaccgggcc atactctggg cggctactca aacagatcg tcgttcatga gcgatatgtt    420
ctgcgtattc gtcacccgca agagcagctg gcggcggtgg ctcctttgtt gtgtgcaggg    480
atcaccacgt attcgccgct acgtcactgg caggccgggc cgggtaaaaa agtgggcgtg    540
gtcggcatcg gcggtctggg acatatgggg attaagctgg cccacgcgat gggggcacat    600
gtggtggcat ttaccacttc tgaggcaaaa cgcgaagcgg caaaagccct gggggccgat    660
gaagttgtta actcacgcaa tgccgatgag atggcggctc atctgaagag tttcgatttc    720
attttgaata cagtagctgc gccacataat ctcgacgatt ttaccacctt gctgaagcgt    780
gatggcacca tgacgctggt tggtgcgcct gcgacaccgc ataaatcgcc ggaagttttc    840
aacctgatca tgaaacgccg tgcgatagcc ggttctatga ttggcggcat tccagaaact    900
caggagatgc tcgattttg cgccaacat ggcatcgtgg ctgatataga gatgattcgg    960
gccgatcaaa ttaatgaagc ctatgagcga atgctgcgcg tgatgtgaa atatcgtttt   1020
gttatcgata atcgcacact aacagac                                      1047
```

<210> SEQ ID NO 13
<211> LENGTH: 365
<212> TYPE: PRT
<213> ORGANISM: Komagataella phaffii

<400> SEQUENCE: 13

```
Met Lys Ile Val Leu Val Leu Tyr Ser Ala Gly Lys His Ala Ala Asp
1               5                   10                  15

Glu Pro Lys Leu Tyr Gly Cys Ile Glu Asn Glu Leu Gly Ile Arg Gln
            20                  25                  30

Trp Leu Glu Lys Gly Gly His Glu Leu Val Thr Thr Ser Asp Lys Glu
        35                  40                  45

Gly Glu Asn Ser Glu Leu Glu Lys His Ile Pro Asp Ala Asp Val Ile
    50                  55                  60

Ile Ser Thr Pro Phe His Pro Ala Tyr Ile Thr Lys Glu Arg Ile Gln
65                  70                  75                  80

Lys Ala Lys Lys Leu Lys Leu Leu Val Val Ala Gly Val Gly Ser Asp
                85                  90                  95

His Ile Asp Leu Asp Tyr Ile Glu Gln Asn Gly Leu Asp Ile Ser Val
            100                 105                 110

Leu Glu Val Thr Gly Ser Asn Val Val Ser Val Ala Glu His Val Val
        115                 120                 125

Met Thr Ile Leu Asn Leu Val Arg Asn Phe Val Pro Ala His Glu Gln
    130                 135                 140

Ile Val Asn His Gly Trp Asp Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Val Ala Phe Asn Pro Lys Glu Leu Leu
            180                 185                 190

Tyr Tyr Asp Tyr Gln Gly Leu Pro Lys Glu Ala Glu Glu Lys Val Gly
```

```
            195                 200                 205
Ala Arg Arg Val Asp Thr Val Glu Glu Leu Val Ala Gln Ala Asp Val
210                 215                 220

Val Thr Val Asn Ala Pro Leu His Ala Gly Thr Lys Gly Leu Val Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Asn Ala Gln Asp Val Ala Asp Ala Val Ala
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Tyr
290                 295                 300

Gly Asn Ala Met Thr Pro His Tyr Ser Gly Thr Thr Leu Asp Ala Gln
305                 310                 315                 320

Val Arg Tyr Ala Glu Gly Thr Lys Asn Ile Leu Asn Ser Phe Leu Thr
                325                 330                 335

Lys Lys Phe Asp Tyr Arg Pro Gln Asp Val Ile Leu Leu Asn Gly Lys
            340                 345                 350

Tyr Lys Thr Lys Ala Tyr Gly Asn Asp Lys Lys Val Ala
        355                 360                 365

<210> SEQ ID NO 14
<211> LENGTH: 261
<212> TYPE: PRT
<213> ORGANISM: Bacillus subtilis

<400> SEQUENCE: 14

Met Tyr Thr Asp Leu Lys Gly Lys Val Val Ala Ile Thr Gly Ala Ser
1               5                   10                  15

Ser Gly Leu Gly Arg Ala Met Ala Ile Arg Phe Gly Gln Glu Gln Ala
            20                  25                  30

Lys Val Val Ile Asn Tyr Tyr Ser Asn Glu Lys Glu Ala Gln Thr Val
        35                  40                  45

Lys Glu Glu Val Gln Lys Ala Gly Gly Glu Ala Val Ile Ile Gln Gly
    50                  55                  60

Asp Val Thr Lys Glu Glu Asp Val Lys Asn Ile Val Gln Thr Ala Val
65                  70                  75                  80

Lys Glu Phe Gly Thr Leu Asp Ile Met Ile Asn Asn Ala Gly Met Glu
                85                  90                  95

Asn Pro Val Glu Ser His Lys Met Pro Leu Lys Asp Trp Asn Lys Val
            100                 105                 110

Ile Asn Thr Asn Leu Thr Gly Ala Phe Leu Gly Cys Arg Glu Ala Ile
        115                 120                 125

Lys Tyr Tyr Val Glu Asn Asp Ile Gln Gly Asn Val Ile Asn Met Ser
    130                 135                 140

Ser Val His Glu Met Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Arg Ile Arg Val Asn Asn Ile Gly Pro Gly Ala Ile Asn
            180                 185                 190

Thr Pro Ile Asn Ala Glu Lys Phe Ala Asp Pro Val Gln Lys Lys Asp
        195                 200                 205
```

```
Val Glu Ser Met Ile Pro Met Gly Tyr Ile Gly Pro Glu Glu Ile
    210                 215                 220

Ala Ala Val Ala Val Trp Leu Ala Ser Lys Glu Ser Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
                260

<210> SEQ ID NO 15
<211> LENGTH: 336
<212> TYPE: PRT
<213> ORGANISM: Pseudomonas abietaniphila

<400> SEQUENCE: 15

Met Leu Pro Lys Leu Val Ile Thr His Arg Val His Asp Glu Ile Leu
1               5                   10                  15

Gln Leu Leu Ala Pro His Cys Glu Leu Met Thr Asn Gln Thr Asp Ser
                20                  25                  30

Thr Leu Thr Arg Glu Glu Ile Leu Arg Arg Cys Arg Asp Ala Gln Ala
            35                  40                  45

Met Met Ala Phe Met Pro Asp Arg Val Asp Ala Asp Phe Leu Gln Ala
50                  55                  60

Cys Pro Glu Leu Arg Val Val Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
                100                 105                 110

Val Gly Leu Gly Arg His Leu Arg Ala Ala Asp Ala Phe Val Arg Ser
            115                 120                 125

Gly Glu Phe Gln Gly Trp Gln Pro Gln Phe Tyr Gly Thr Gly Leu Asp
            130                 135                 140

Asn Ala Thr Val Gly Ile Leu Gly Met Gly Ala Ile Gly Leu Ala Met
145                 150                 155                 160

Ala Asp Arg Leu Gln Gly Trp Gly Ala Thr Leu Gln Tyr His Glu Ala
                165                 170                 175

Lys Ala Leu Asp Thr Gln Thr Gln Arg Leu Gly Leu Arg Gln Val
                180                 185                 190

Ala Cys Ser Glu Leu Phe Ala Ser Asp Phe Ile Leu Leu Ala Leu
                195                 200                 205

Pro Leu Asn Ala Asp Thr Gln His Leu Val Asn Ala Glu Leu Leu Ala
                210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
                260                 265                 270

Arg Pro Arg Leu Ile Asp Pro Ala Leu Leu Ala His Pro Asn Thr Leu
            275                 280                 285

Phe Thr Pro His Ile Gly Ser Ala Val Arg Ala Val Arg Leu Glu Ile
        290                 295                 300

Glu Arg Cys Ala Ala Gln Asn Ile Ile Gln Val Leu Ala Gly Ala Arg
305                 310                 315                 320
```

Pro Ile Asn Ala Ala Asn Arg Leu Pro Lys Ala Glu Pro Ala Ala Cys
            325                 330                 335

<210> SEQ ID NO 16
<211> LENGTH: 1095
<212> TYPE: DNA
<213> ORGANISM: Komagataella phaffii

<400> SEQUENCE: 16

| | | | | | |
|---|---|---|---|---|---|
| atgaaaatcg | ttctcgtttt | gtactccgct | ggtaagcacg | ccgccgatga | accaaagttg | 60 |
| tatggttgta | tcgaaaatga | attgggtatt | agacaatggc | ttgagaaggg | cggccatgaa | 120 |
| ttggttacta | catcagacaa | agagggtgaa | aactctgagt | tagaaaagca | cattcctgac | 180 |
| gctgatgtga | ttatttccac | tccattccat | ccagcctaca | tcacgaagga | gagaatccaa | 240 |
| aaagccaaga | agctgaagtt | gttggtcgtt | gctggtgtcg | gttccgacca | cattgacttg | 300 |
| gactacattg | aacaaaatgg | cctagatatt | tcggtcctag | aggttactgg | ttccaacgtt | 360 |
| gtttcagtgg | ctgagcatgt | cgttatgact | atattgaact | ggtgagaaa | ctttgttcca | 420 |
| gctcacgagc | aaattgttaa | ccacggctgg | gacgttgctg | ccatcgccaa | ggacgcctac | 480 |
| gatatcgaag | taagaccat | cgcaacaatt | ggtgctggaa | gaattggtta | cagagtctta | 540 |
| gagagacttg | tggctttcaa | ccctaaggaa | ttgttgtact | acgactacca | aggtcttcca | 600 |
| aaagaggccg | aggaaaaagt | tggtgccaga | gagtcgaca | ctgtcgagga | gctggttgct | 660 |
| caagccgatg | ttgttaccgt | caatgcccca | ctgcacgcag | gtactaaggg | tttagttaac | 720 |
| aaggagcttc | tgtccaagtt | caagaagggt | gcttggttgg | ttaacacagc | cagaggtgcc | 780 |
| atctgcaatg | ctcaagatgt | cgctgatgcc | gttgcatctg | gtcaattgag | aggttacggt | 840 |
| ggtgacgtct | ggttccctca | gccagctcca | aaggaccatc | catggagaga | tatgagaaac | 900 |
| aagtacggat | acggaaacgc | catgactcct | cattactcag | gtaccacttt | ggacgcccag | 960 |
| gtcagatatg | ccgaaggtac | caagaacatc | ttgaactcat | tccttaccaa | gaagtttgac | 1020 |
| tacagacctc | aagatgtcat | tcttttgaac | ggtaagtaca | agaccaaggc | ttatggtaat | 1080 |
| gacaaaaagg | tcgca | | | | | 1095 |

<210> SEQ ID NO 17
<211> LENGTH: 784
<212> TYPE: DNA
<213> ORGANISM: Bacillus subtilis

<400> SEQUENCE: 17

| | | | | | |
|---|---|---|---|---|---|
| atgtacacgg | atctaaaagg | aaaagtcgtt | gccattacag | gagcatcatc | aggattagga | 60 |
| agagcgatgg | cgatccgctt | cgggcaggag | caggcgaaag | tcgtgattaa | ctactacagt | 120 |
| aatgaaaaag | aggctcaaac | cgtaaaagaa | gaagttcaaa | aagcgggcgg | cgaagcggtc | 180 |
| attattcaag | gtgacgttac | aaaagaagag | gatgtcaaaa | acattgtgca | gaccgcggtc | 240 |
| aaggaattcg | gcacattaga | tatcatgatc | aacaacgccg | gcatggaaaa | tccggtcgag | 300 |
| tcgcataaaa | tgccgctaaa | agactggaac | aaagtcatca | caccaacct | gaccggcgct | 360 |
| tttctgggat | gccgcgaagc | cattaaatat | acgtagaga | atgatattca | aggaaacgtc | 420 |
| attaacatgt | cgagcgtaca | tgaaatgatt | ccgtggccgc | tgtttgtcca | ctatgcggca | 480 |
| agtaaaggcg | gcattaaatt | aatgacggaa | acattggcgc | ttgagtacgc | gccgaagcgc | 540 |
| atccgtgtta | acaatatcgg | gccgggcgcc | atcaatacgc | cgatcaatgc | ggaaagtttt | 600 |
| gcggatcccg | ttcagaaaaa | agatgtggaa | agcatgattc | cgatggggta | tatcggtgag | 660 |

-continued

```
ccggaagaaa tcgcggctgt cgccgtctgg cttgcttcaa aggaatcaag ctacgtgacc    720
ggcattacgc tgtttgctga cggcggaatg acacaatatc cgtcattcca ggcaggccgc    780
ggat                                                                 784

<210> SEQ ID NO 18
<211> LENGTH: 1008
<212> TYPE: DNA
<213> ORGANISM: Pseudomonas abietaniphila

<400> SEQUENCE: 18
atgctgccga aactcgttat aactcaccga gtacacgatg agatcctgca actgctggcg     60
ccacattgcg agctgatgac caaccagacc gacagcacgc tgacgcgcga ggaaattctg    120
cgccgctgcc gcgatgctca ggcgatgatg gcgttcatgc ccgatcgggt cgatgcagac    180
tttcttcaag cctgccctga gctgcgtgta gtcggctgcg cgctcaaggg cttcgacaat    240
ttcgatgtgg acgcctgtac tgcccgcggg gtctggctga ccttcgtgcc tgatctgttg    300
acggtcccga ctgccgagct ggcgatcgga ctggcggtgg ggctggggcg gcatctgcgg    360
gcagcagatg cgttcgtccg ctctggcgag ttccagggct ggcaaccaca gttctacggc    420
acggggctgg ataacgctac ggtcggcatc cttggcatgg gcgccatcgg actggccatg    480
gctgatcgct tgcagggatg gggcgcgacc ctgcagtacc acgaggcgaa ggctctggat    540
acacaaaccg agcaacggct cggcctgcgc caggtggcgt gcagcgaact cttcgccagc    600
tcggacttca tcctgctggc gcttcccttg aatgccgata cccagcatct ggtcaacgcc    660
gagctgcttg ccctcgtacg gccgggcgct ctgcttgtaa acccctgtcg tggttcggta    720
gtggatgaag ccgccgtgct cgcggcgctt gagcgaggcc agctcggcgg gtatgcggcg    780
gatgtattcg aaatggaaga ctgggctcgc gcggaccggc cgcggctgat cgatcctgcg    840
ctgctcgcgc atccgaatac gctgttcact ccgcacatag ggtcggcagt gcgcgcggtg    900
cgcctggaga ttgaacgttg tgcagcgcag aacatcatcc aggtattggc aggtgcgcgc    960
ccaatcaacg ctgcgaaccg tctgcccaag gccgagcctg ccgcatgt              1008
```